(12) United States Patent
Yang et al.

(10) Patent No.: US 12,350,301 B2
(45) Date of Patent: Jul. 8, 2025

(54) **COMPOSITION COMPRISING THREE *LACTOBACILLUS* SP. STRAINS, AND USE THEREOF**

(71) Applicant: GI BIOME INC., Seongnam-si (KR)

(72) Inventors: Bo Gie Yang, Seoul (KR); Myung Ho Jang, Seoul (KR); Han Sung Lee, Seongnam-si (KR)

(73) Assignee: GI BIOME INC., Seongnam-si (KR)

( * ) Notice: Subject to any disclaimer, the term of this patent is extended or adjusted under 35 U.S.C. 154(b) by 0 days.

(21) Appl. No.: 18/270,925

(22) PCT Filed: Jun. 30, 2022

(86) PCT No.: PCT/KR2022/009479
§ 371 (c)(1),
(2) Date: Jul. 5, 2023

(87) PCT Pub. No.: WO2023/277638
PCT Pub. Date: Jan. 5, 2023

(65) Prior Publication Data
US 2024/0050495 A1    Feb. 15, 2024

(30) Foreign Application Priority Data

Jun. 30, 2021  (KR) .................. 10-2021-0086148
Jun. 30, 2022  (KR) .................. 10-2022-0080568

(51) Int. Cl.
| | | |
|---|---|---|
| *A61K 35/747* | (2015.01) | |
| *A61P 3/04* | (2006.01) | |
| *A61P 21/00* | (2006.01) | |
| *A61P 39/06* | (2006.01) | |
| *C12N 1/20* | (2006.01) | |
| *C12R 1/25* | (2006.01) | |

(52) U.S. Cl.
CPC .............. *A61K 35/747* (2013.01); *A61P 3/04* (2018.01); *A61P 21/00* (2018.01); *A61P 39/06* (2018.01); *C12N 1/205* (2021.05); *C12R 2001/25* (2021.05)

(58) Field of Classification Search
None
See application file for complete search history.

(56) References Cited

U.S. PATENT DOCUMENTS

| | | | | |
|---|---|---|---|---|
| 2009/0170185 A1* | 7/2009 | Hayakawa | ................ | A61P 3/06 435/252.1 |
| 2015/0238549 A1* | 8/2015 | Brudnak | ............... | A61K 9/0031 424/93.4 |
| 2019/0070229 A1* | 3/2019 | Choi | .................... | A61K 9/0034 |

FOREIGN PATENT DOCUMENTS

| | | |
|---|---|---|
| CN | 104127443 A | 11/2014 |
| CN | 104187634 A | 12/2014 |
| CN | 111876356 A | 11/2020 |
| CN | 112586744 A | 4/2021 |
| KR | 10-2016-0098149 A | 8/2016 |
| KR | 10-2016-0098955 A | 8/2016 |
| KR | 10-1938801 B1 | 1/2019 |
| KR | 10-1938865 B1 | 1/2019 |
| KR | 10-1981333 B1 | 5/2019 |
| KR | 10-2049700 B1 | 11/2019 |
| KR | 10-2019-0135764 A | 12/2019 |
| KR | 10-2020-0034169 A | 3/2020 |
| KR | 10-2021-0058729 A | 5/2021 |
| KR | 10-2021-0067689 A | 6/2021 |
| KR | 10-2021-0086537 A | 7/2021 |
| KR | 10-2021-0086539 A | 7/2021 |
| KR | 10-2021-0086540 A | 7/2021 |
| KR | 10-2021-0152670 A | 12/2021 |
| WO | 2019/157585 A1 | 8/2019 |
| WO | 2020/080736 A1 | 4/2020 |
| WO | 2020/260958 A1 | 12/2020 |
| WO | 2021/137600 A1 | 7/2021 |

OTHER PUBLICATIONS

Tsai et al., "Gerobiotics: probiotics targeting fundamental aging processes", Bioscience of Microbiota, Food, and Health, vol. 40(1), pp. 1-11. (Year: 2021).*
Jung, J., et al., "Fermentation of red ginseng extract by the probiotic Lactobacillus plantarum KCCM 11613P: ginsenoside conversion and antioxidant effects", Journal of Ginseng Research, vol. 43, pp. 20-26. (Year: 2019).*
Kim, J.Y., et al., "Probiotic Potential of a Novel Vitamin B2-Overproducing Lactobacillus plantarum Strain, HY7715, Isolated from Kimchi", Applied Sciences, vol. 11, pp. 1-18. (Year: 2021).*
Zhongmei He, et al., "Antioxidant activity of prebiotic ginseng polysaccharides combined with potential probiotic Lactobacillus plantarum C88", International Journal of Food Science and Technology, vol. 50, 2015, pp. 1673-1682.
Dana Binyamin, et al., "The aging mouse microbiome has obesogenic characteristics", Genome Medicine, vol. 12, No. 87, 2020, pp. 1-9.
Dayoung Kang, et al., "Anti-Obesity Effects of a Mixture of Fermented Ginseng, Bifidobacterium longum BORI, and Lactobacillus paracasei CH88 in High-Fat Diet-Fed Mice", J. Microbiol. Biotechnol., vol. 28, No. 5, 2018, pp. 688-696.
Patrick D. Schloss, et al., "Introducing mothur: Open-Source, Platform-Independent, Community-Supported Software for Describing and Comparing Microbial Communities", Appl. Environ. Microbiol., vol. 75, No. 23, 2009, pp. 7537-7541.

(Continued)

*Primary Examiner* — Michelle F. Paguio Frising
*Assistant Examiner* — Grant C Currens
(74) *Attorney, Agent, or Firm* — Sughrue Mion, PLLC

(57) ABSTRACT

Provided are a mixture of three species of *Lactobacillus fermentum* strain and *Lactobacillus plantarum* strain and use thereof. A composition according to one aspect including, as an active ingredient, a mixture of *Lactobacillus fermentum* strains GB102 and GB103 and *Lactobacillus plantarum* strain GB104; or a lysate or culture solution thereof, or an extract of the culture solution, can be usefully used for the prevention or treatment of muscle-related disorders or obesity by alleviating the decrease in grip strength induced by aging or reducing the change in intestinal microbial environment induced by aging.

14 Claims, 5 Drawing Sheets

Specification includes a Sequence Listing.

(56) References Cited

OTHER PUBLICATIONS

Muriel Giron, et al., "Gut microbes and muscle function: can probiotics make our muscles stronger?", Journal of Cachexia, Sarcopenia and Muscle, vol. 13, 2022, pp. 1460-1476.
Notice of Non-Final Rejection for KR 10-2022-0080568 dated Sep. 28, 2022.
Decision to grant a patent for KR 10-2022-0080568 dated Feb. 20, 2023.
International Search Report for PCT/KR2022/009479 dated Oct. 17, 2022.
Search Report for TW111124631 dated Aug. 3, 2023.
Australian Patent Office, Office Action issued Jun. 4, 2024 in copending Application No. 2022302837.
Extended European Search Report dated Dec. 13, 2024 from the European Patent Office in Application No. 22833691.3.

\* cited by examiner

COMPOSITION COMPRISING THREE *LACTOBACILLUS* SP. STRAINS, AND USE THEREOF

CROSS REFERENCE TO RELATED APPLICATIONS

This application is a National Stage of International Application No. PCT/KR2022/009479 filed Jun. 30, 2022, claiming priority based on Korean Patent Application No. 10-2021-0086148 filed Jun. 30, 2021 and Korean Patent Application No. 10-2022-0080568 filed Jun. 30, 2022, the entire disclosures of which are incorporated herein by reference.

INCORPORATION BY REFERENCE OF SEQUENCE LISTING

The content of the electronically submitted sequence listing, file name: Q287968_sequence listing as filed. TXT; size: 7,044 bytes; and date of creation: May 19, 2023, filed herewith, is incorporated herein by reference in its entirety.

TECHNICAL FIELD

The present disclosure relates to a composition including 3 strains of *Lactobacillus* sp. and use thereof.

BACKGROUND ART

The microbiome refers to the microflora present in a specific environment and their entire biological information, including the genetic information of the microflora within corresponding environment and the collection of all the derived products (genome, transcriptome, proteome, metabolome). Therefore, the human microbiome refers to the microflora inhabiting inside and outside of the human body and entire biological information thereof.

The human body has symbiotic relationships with many microorganisms, and especially the inside of the intestine is an environment which is optimal for microflora to consume nutrients and to form a systematic cluster. Many microflora exist in the intestine. Intestinal microflora supply nutrients that cannot be produced by the host's own enzymes alone, and are closely related to the host's metabolism and immune system, and have been reported to be associated with various diseases such as irritable bowel syndrome, obesity, atopy, depression, rheumatoid arthritis, autism spectrum disorder, and dementia.

Recently, due to Western dietary habits and indiscriminate use of antibiotics, imbalances in the intestinal microflora occur, leading to deteriorating intestine health, and research into the relationship between intestinal microflora and various diseases has highlighted the importance of intestinal microflora and raised interest in the subject.

Furthermore, with the increase in average human lifespan, aging societies are facing various challenges that have never been in front of the mankind. Socioeconomically, due to the increase in the aging population and a decrease in the working-age population, the elderly population support ratio per capita is expected to increase, and interest in improving the quality of life of the elderly is also increasing. As social demand for a healthy and happy life in the elderly increases, research is actively underway into changes in disease patterns due to aging and the prevention of age-related diseases.

As interest in *Lactobacillus* has recently increased, research results confirming the usefulness of *Lactobacillus* for the prevention and treatment of aging-related disorders have been reported. Korean Patent Registration No. 10-2049700 is a patent that discloses the activity of preventing or treating muscle diseases of the *Lactobacillus reuteri* ATG-F4 strain, but it is an invention using each single strain as an active ingredient. That is, there is currently no invention disclosed that uses a mixed strain as an active ingredient. Therefore, the present inventors tried to discover strains for the use of compositions applicable to food and medicine.

DETAILED DESCRIPTION OF THE DISCLOSURE

Technical Problem

An aspect provides a composition including at least one, two, or three or more selected from the group consisting of: one of a *Lactobacillus fermentum* GB102 strain belonging to *Lactobacillus* sp. deposited with accession number KCTC 14105BP, a lysate thereof, and a culture solution thereof; one of a *Lactobacillus fermentum* GB103 strain belonging to *Lactobacillus* sp. deposited with accession number KCTC 14106BP, a lysate thereof, and a culture solution thereof; and one of a *Lactobacillus plantarum* GB104 strain belonging to *Lactobacillus* sp. deposited with accession number KCTC 14107BP, a lysate thereof, and a culture solution thereof.

Another aspect is to provide an anti-aging or antioxidant composition containing, as an active ingredient, a composition including at least one, two, or three or more selected from the group consisting of: one of a *Lactobacillus fermentum* GB102 strain belonging to *Lactobacillus* sp. deposited with accession number KCTC 14105BP, a lysate thereof, and a culture solution thereof; one of a *Lactobacillus fermentum* GB103 strain belonging to *Lactobacillus* sp. deposited with accession number KCTC 14106BP, a lysate thereof, and a culture solution thereof; and one of a *Lactobacillus plantarum* GB104 strain belonging to *Lactobacillus* sp. deposited with accession number KCTC 14107BP, a lysate thereof, and a culture solution thereof.

Another aspect is to provide a composition for preventing, alleviating or treating aging-related disorders containing, as an active ingredient, a composition including at least one, two, or three or more selected from the group consisting of: one of a *Lactobacillus fermentum* GB102 strain belonging to *Lactobacillus* sp. deposited with accession number KCTC 14105BP, a lysate thereof, and a culture solution thereof; one of a *Lactobacillus fermentum* GB103 strain belonging to *Lactobacillus* sp. deposited with accession number KCTC 14106BP, a lysate thereof, and a culture solution thereof; and one of a *Lactobacillus plantarum* GB104 strain belonging to *Lactobacillus* sp. deposited with accession number KCTC 14107BP, a lysate thereof, and a culture solution thereof.

Another aspect is to provide a method of inhibiting aging including administering an effective amount of the composition to a subject in need thereof.

Another aspect is to provide use of the composition for the manufacture of an anti-aging composition.

Another aspect is to provide a health functional food for preventing or alleviating muscle-related disorders or obesity containing, as an active ingredient, a composition including at least one, two, or three or more selected from the group consisting of: one of a *Lactobacillus fermentum* GB102 strain belonging to *Lactobacillus* sp. deposited with accession number KCTC 14105BP, a lysate thereof, and a culture solution thereof; one of a *Lactobacillus fermentum* GB103 strain belonging to *Lactobacillus* sp. deposited with accession number KCTC 14106BP, a lysate thereof, and a culture solution thereof; and one of a *Lactobacillus plantarum* GB104 strain belonging to *Lactobacillus* sp. deposited with accession number KCTC 14107BP, a lysate thereof, and a culture solution thereof.

Another aspect is to provide a pharmaceutical composition for prevention or treatment of muscle-related disorders or obesity containing, as an active ingredient, a composition including at least one, two, or three or more selected from the group consisting of: one of a *Lactobacillus fermentum* GB102 strain belonging to *Lactobacillus* sp. deposited with accession number KCTC 14105BP, a lysate thereof, and a culture solution thereof; one of a *Lactobacillus fermentum* GB103 strain belonging to *Lactobacillus* sp. deposited with accession number KCTC 14106BP, a lysate thereof, and a culture solution thereof; and one of a *Lactobacillus plantarum* GB104 strain belonging to *Lactobacillus* sp. deposited with accession number KCTC 14107BP, a lysate thereof, and a culture solution thereof.

Another aspect is to provide a method of preventing or treating muscle-related disorders including administering an effective amount of the composition to a subject in need thereof.

Another aspect is to provide use of the composition for the manufacture of health functional food for preventing or alleviating muscle-related disorders.

Another aspect is to provide a method of preventing or treating obesity including administering an effective amount of the composition to a subject in need thereof.

Another aspect is to provide use of the composition for the manufacture of health functional food for preventing or alleviating obesity.

Another aspect is to provide use of the composition for the manufacture of pharmaceutical preparation for preventing or treating muscle-related disorders.

Another aspect is to provide use of the composition for the manufacture of pharmaceutical preparation for preventing or treating obesity.

Another aspect is to provide a feed composition containing, as an active ingredient, a composition including at least one, two, or three or more selected from the group consisting of: one of a *Lactobacillus fermentum* GB102 strain belonging to *Lactobacillus* sp. deposited with accession number KCTC 14105BP, a lysate thereof, and a culture solution thereof; one of a *Lactobacillus fermentum* GB103 strain belonging to *Lactobacillus* sp. deposited with accession number KCTC 14106BP, a lysate thereof, and a culture solution thereof; and one of a *Lactobacillus plantarum* GB104 strain belonging to *Lactobacillus* sp. deposited with accession number KCTC 14107BP, a lysate thereof, and a culture solution thereof.

Technical Solution to Problem

An aspect provides a composition including at least one, two, or three or more selected from the group consisting of: one of a *Lactobacillus fermentum* GB102 strain belonging to *Lactobacillus* sp. deposited with accession number KCTC 14105BP, a lysate thereof, and a culture solution thereof; one of a *Lactobacillus fermentum* GB103 strain belonging to *Lactobacillus* sp. deposited with accession number KCTC 14106BP, a lysate thereof, and a culture solution thereof; and one of a *Lactobacillus plantarum* GB104 strain belonging to *Lactobacillus* sp. deposited with accession number KCTC 14107BP, a lysate thereof, and a culture solution thereof.

In an embodiment, the strain in the composition may be live bacteria or dead bacteria.

In an embodiment, a mixed strain included in the composition may be included in an amount of $10^3$ CFU/g to $10^{16}$ CFU/g.

In an embodiment, the composition may be administered orally.

Another aspect is to provide an anti-aging composition, an antioxidant composition, or a composition for preventing, alleviating or treating aging-related disorders containing, as an active ingredient, a composition including at least one, two, or three or more selected from the group consisting of: one of a *Lactobacillus fermentum* GB102 strain belonging to *Lactobacillus* sp. deposited with accession number KCTC 14105BP, a lysate thereof, and a culture solution thereof; one of a *Lactobacillus fermentum* GB103 strain belonging to *Lactobacillus* sp. deposited with accession number KCTC 14106BP, a lysate thereof, and a culture solution thereof; and one of a *Lactobacillus plantarum* GB104 strain belonging to *Lactobacillus* sp. deposited with accession number KCTC 14107BP, a lysate thereof, and a culture solution thereof.

In an embodiment, the anti-aging may be one or more selected from the group consisting of anti-aging of muscle cells, anti-aging of nerve cells, anti-aging of skin cells, and anti-aging of the intestinal microbial environment.

Another aspect provides a health functional food for preventing or alleviating muscle-related disorders or obesity containing, as an active ingredient, a composition including at least one, two, or three or more selected from the group consisting of: one of a *Lactobacillus fermentum* GB102 strain belonging to *Lactobacillus* sp. deposited with accession number KCTC 14105BP, a lysate thereof, and a culture solution thereof; one of a *Lactobacillus fermentum* GB103 strain belonging to *Lactobacillus* sp. deposited with accession number KCTC 14106BP, a lysate thereof, and a culture solution thereof; and one of a *Lactobacillus plantarum* GB104 strain belonging to *Lactobacillus* sp. deposited with accession number KCTC 14107BP, a lysate thereof, and a culture solution thereof.

In an embodiment, the composition may reduce at least one from the group consisting of joint stiffness, muscle loss, power loss, speed loss, balance loss, endurance loss, and agility loss.

In an embodiment, the composition may cause at least one selected from the group consisting of increasing exercise performance, restoring muscle coordination, mobility and gait, and increasing muscle mass and grip strength.

In an embodiment, the pharmaceutical composition for preventing or treating muscle-related disorders may increase exercise performance, restore muscle coordination, mobility and gait, increase muscle mass and strength, or inhibit grip strength loss of the elderly.

In an embodiment, the muscle-related disorders may be one or more selected from the group consisting of sarcopenia, geriatric sarcopenia, muscular atrophy, muscular dystrophy, disuse muscle atrophy, motor neuron disease, inflammatory myopathy, neuromuscular junction disease, endocrine myopathy, muscle degeneration, myotonia, muscular atrophy with progressive sclerosis, myasthenia gravis, myositis, muscle calcification, muscle ossification, muscle weakness-related disorders, and cachexia.

Another aspect provides a pharmaceutical composition for the prevention or treatment of muscle-related disorders or obesity containing, as an active ingredient, a composition including at least one, two, or three or more selected from the group consisting of: one of a *Lactobacillus fermentum* GB102 strain belonging to *Lactobacillus* sp. deposited with accession number KCTC 14105BP, a lysate thereof, and a culture solution thereof; one of a *Lactobacillus fermentum*

GB103 strain belonging to *Lactobacillus* sp. deposited with accession number KCTC 14106BP, a lysate thereof, and a culture solution thereof; and one of a *Lactobacillus plantarum* GB104 strain belonging to *Lactobacillus* sp. deposited with accession number KCTC 14107BP, a lysate thereof, and a culture solution thereof.

In an embodiment, the composition may reduce at least one from the group consisting of joint stiffness, muscle loss, power loss, speed loss, balance loss, endurance loss, and agility loss.

In an embodiment, the composition may cause at least one selected from the group consisting of increasing exercise performance, restoring muscle coordination, mobility and gait, and increasing muscle mass and strength.

In an embodiment, the muscle-related disorders may be one or more selected from the group consisting of sarcopenia, geriatric sarcopenia, muscular atrophy, muscular dystrophy, disuse muscle atrophy, motor neuron disease, inflammatory myopathy, neuromuscular junction disease, endocrine myopathy, muscle degeneration, myotonia, muscular atrophy with progressive sclerosis, myasthenia gravis, myositis, muscle calcification, muscle ossification, muscle weakness-related disorders, and cachexia.

Advantageous Effects of Disclosure

A composition according to an aspect including, as an active ingredient, a mixture of *Lactobacillus fermentum* strains GB102 and GB103 and *Lactobacillus plantarum* strain GB104, a lysate or culture solution thereof, or an extract of the culture solution, can be used beneficially for the prevention or treatment of muscle-related disorders or obesity, for example, by reducing the decrease in grip strength induced by aging and reducing changes in the intestinal microflora induced by aging.

BEST MODE

Figure 1:
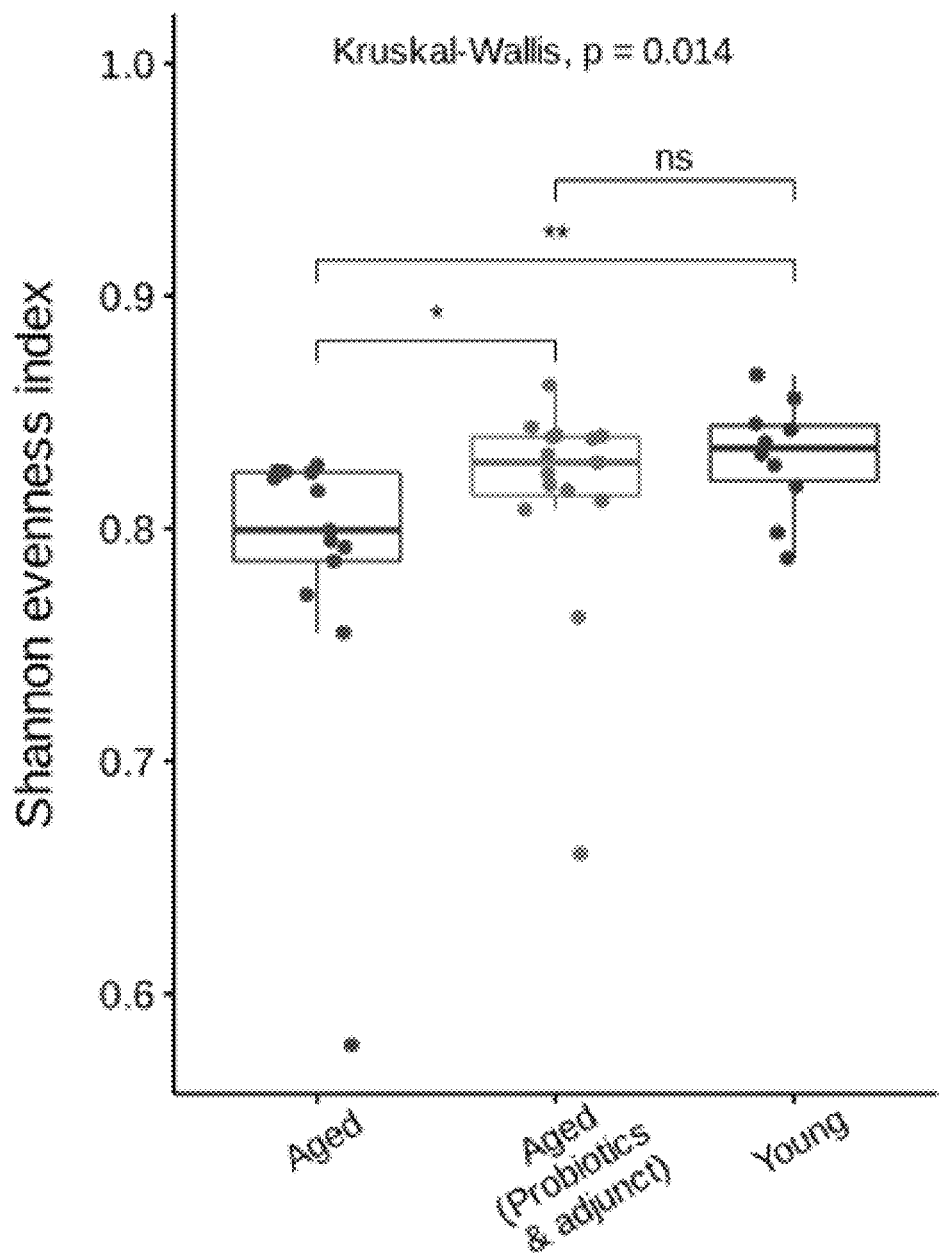
FIG. 1 shows the graph of the change in the evenness of the flora according to the co-administration of mixed strain and herbal medicines according to an embodiment.

An aspect provides a composition including at least one, two, or three or more selected from the group consisting of: one of a *Lactobacillus fermentum* GB102 strain belonging to *Lactobacillus* sp. deposited with accession number KCTC 14105BP, a lysate thereof, and a culture solution thereof; one of a *Lactobacillus fermentum* GB103 strain belonging to *Lactobacillus* sp. deposited with accession number KCTC 14106BP, a lysate thereof, and a culture solution thereof; and one of a *Lactobacillus plantarum* GB104 strain belonging to *Lactobacillus* sp. deposited with accession number KCTC 14107BP, a lysate thereof, and a culture solution thereof.

In an embodiment, the *Lactobacillus fermentum* GB102 strain, the *Lactobacillus fermentum* GB103 strain, and the *Lactobacillus plantarum* GB104 strain may be live bacteria or dead bacteria. Specifically, the dead bacteria may be dead bacteria caused by heat treatment.

*Lactobacillus* sp. used herein refers to the old *Lactobacillus* sp. before the change in the name including *Lactiplantibacillus plantarum* and Limosi *Lactobacillus fermentum*.

The *Lactobacillus* has been renamed as *Limosilactobacillus* or *Lactiplantibacillus*, and the changed strain names may be used interchangeably herein. For example, the strain name of *Lactobacillus fermentum* was changed to *Limosilactobacillus fermentum*, and the strain name of *Lactobacillus plantarum* was changed to *Lactiplantibacillus plantarum*.

The term "culture" may be used interchangeably with "culture supernatant," "conditioned culture medium" or "conditioned medium," and may refer to the entire medium including a strain obtained by culturing the strain in a medium for a certain period of time, metabolites thereof, extra nutrients, and the like, wherein the medium is capable of supplying nutrients to allow growth and survival of the *Lactobacillus* strain in the test tube. In addition, the culture solution may refer to a culture solution obtained by removing cells from a cell culture solution obtained by culturing a strain. The medium may be selected from known liquid medium or solid medium, and may be, for example, an MRS liquid medium, a GAM liquid medium, an MRS agar medium, a GAM agar medium, and a BL agar medium, but is not limited thereto.

The term "lysate" refers to a solution or suspension in an aqueous medium of cells of a microflora such as broken *Lactobacillus fermentum* or *Lactobacillus plantarum*. A cell lysate contains, for example, macromolecules such as DNA, RNA, proteins, peptides, carbohydrates, lipids, etc. and/or micromolecules such as amino acids, sugars, fatty acids, etc., or fractions thereof. In addition, the lysate contains cell debris, which may be smooth or granular.

As a method capable of achieving cell lysis of the microflora, various known methods may be used, and any method capable of achieving cell lysis of the microflora may be used. For example, cell opening/disruption may be performed enzymatically, chemically or physically. Non-limiting examples of enzymes and mixtures of enzymes are proteases such as proteinase K, Lipases, or glycosidases; non-limiting examples of chemicals are ionophores, detergents such as sodium dodecyl sulfate, acids or bases; and non-limiting examples of physical means are high pressure such as French pressing, osmotic pressure, or temperature such as heat or cold. In addition, a method using an appropriate combination of enzymes other than proteolytic enzymes, acids, bases, and the like may also be used.

The culture solution may include a culture solution itself obtained by culturing the strain, a concentrate thereof, or a lyophilisate thereof, or a culture supernatant obtained by removing the strain from the culture solution, a concentrate thereof, or a lyophilisate thereof.

Another aspect is to provide an anti-aging or antioxidant composition containing, as an active ingredient, a composition including at least one, two, or three or more selected from the group consisting of: one of a *Lactobacillus fermentum* GB102 strain belonging to *Lactobacillus* sp. deposited with accession number KCTC 14105BP, a lysate thereof, and a culture solution thereof; one of a *Lactobacillus fermentum* GB103 strain belonging to *Lactobacillus* sp. deposited with accession number KCTC 14106BP, a lysate thereof, and a culture solution thereof; and one of a *Lactobacillus plantarum* GB104 strain belonging to *Lactobacillus* sp. deposited with accession number KCTC 14107BP, a lysate thereof, and a culture solution thereof.

The wording "containing, as an active ingredient" used herein refers to the addition of a strain of *Lactobacillus* sp., vesicles derived from the strain, a lysate of the strain, a culture solution, or an extract of the culture solution, and includes formulation into various forms by adding various components as subcomponents for drug delivery and stabilization.

The term "therapeutically effective amount" used herein refers to an amount of a mixed strain composition for the methods and uses of the present disclosure or a pharmaceutical composition including a mixed strain for the method and use of the present invention, which results in biological or medical responses or desired therapeutic effects in patients that researchers, physicians, or other clinicians seek to achieve. A therapeutically effective amount of a mixed strain composition may vary depending on factors such as the disease state, age, sex, and weight of the subject. A therapeutically effective amount also refers to such an amount at which the therapeutic benefit exceeds any toxicity or harmful effects.

Another aspect is to provide a composition for preventing, alleviating, or treating aging-related disorders containing, as an active ingredient, a composition including at least one, two, or three or more selected from the group consisting of: one of a *Lactobacillus fermentum* GB102 strain belonging to *Lactobacillus* sp. deposited with accession number KCTC 14105BP, a lysate thereof, and a culture solution thereof; one of a *Lactobacillus fermentum* GB103 strain belonging to *Lactobacillus* sp. deposited with accession number KCTC 14106BP, a lysate thereof, and a culture solution thereof; and one of a *Lactobacillus plantarum* GB104 strain belonging to *Lactobacillus* sp. deposited with accession number KCTC 14107BP, a lysate thereof, and a culture solution thereof.

In an embodiment, a mixed strain or mixed strain composition of *Lactobacillus* sp. may have antioxidant activity. Without being limited by any particular theory, the natural process of aging makes the body more susceptible to oxidative damage. Anti-aging effects are mostly related to antioxidant properties and free radical scavenging abilities. Further, without being bound by any particular theory, oxidative damage has been proposed as one of the major causes of skeletal muscle decline that occurs with aging. The identification of free radicals as accelerators of the aging process refers to that inhibition of the same can limit the harmful modifications they exert on organisms (particularly skeletal muscle). In other words, when molecules with antioxidant capacity are able to counteract oxidative damage, such molecules could play an important role in preventing the development of aging-related conditions, including the neutralization process. Oxidative damage underlies the pathophysiological mechanism that causes sarcopenia (and other senile diseases), and interventions to enhance endogenous antioxidant defenses (for example, administration of antioxidants) result in inhibition of aging. For example, it has been reported that resveratrol, a polyphenolic compound contained in red wine, can slow down the aging of *Caenorhabditis elegans* due to reduced mitochondrial respiration (Wood et al., 2004). In addition, oxidative stress has been shown to increase bone turnover by causing an imbalance between cells responsible for bone formation and cells responsible for bone resorption. Therefore, since antioxidants are known to inhibit and/or improve the effects of oxidative stress, a mixed strain of *Lactobacillus* sp. according to an embodiment exhibiting antioxidant activity is useful for anti-aging or prevention, alleviation, or treatment of age-related diseases.

In an embodiment, administration of the mixed strain composition of the genus *Lactobacillus* can increase grip strength that has been decreased due to aging. Specifically, in an embodiment of the present disclosure, it was confirmed that the grip strength increased in the group of aging mice administered with the mixed strain composition of *Lactobacillus* sp. was administered.

In an embodiment, administration of the mixed strain composition of *Lactobacillus* sp. may alleviate changes in the intestinal microbial environment due to aging. In an embodiment, it was confirmed that administration of the mixed strain composition of the genus *Lactobacillus* changes the intestinal flora of the aging mice to be similar to that of the young mouse, thereby preventing or treating aging-related disorders, such as obesity, caused by the intestinal flora of the aging mice. In a recent paper, it was reported that the intestinal flora of aging mice can induce obesity, and that the ratio of Firmicutes/Bacteroidetes is increased in aging mice (Binyamin et al., Genome Medicine, 2020). This suggests that the administration of the *Lactobacillus* mixed strain composition according to an embodiment may have a positive effect on the prevention and treatment of diseases such as obesity in aging mice.

The term "anti-aging" used herein includes delaying or preventing aging of a cell or a subject, or converting a senescent cell into a younger cell.

In an embodiment, the anti-aging may be one or more selected from the group consisting of anti-aging of skeletal muscle cells, anti-aging of nerve cells, anti-aging of skin cells, anti-aging of immune cells, and anti-aging of the intestinal microbial environment.

Aging-related disorders in the present specification may be muscle aging-related disorders (for example, sarcopenia) or obesity.

Aging affects not only a single cell in the body but also every tissue and organ in the body. With aging, wrinkles on the skin increase, the waist bends, and the body composition ratio changes. With aging, the composition ratio of water, muscle protein, fat, and minerals that make up the bone skeleton changes. When compared with a 25-year-old young man, a 70-year-old old man has a decrease in water, muscle mass, and minerals, but a two-fold increase in fat. Changes in body fat according to age are directly related to geriatric diseases. Fat does not only increase in proportion, but also changes in distribution. Thus, subcutaneous fat is decreased and abdominal visceral fat is increased. Although the reason has yet to be clearly identified, visceral fat secretes more harmful cytokines such as TNF-α and IL-6, which cause adult diseases such as diabetes and hypertension, and diminishes many physiological functions.

In addition, muscle mass decreases after the age of 30, and a decrease in growth hormone or male hormone affects the decrease in muscle mass. In general, it is known that after the age of 50, muscle mass decreases by 1%-2% each year, and grip strength decreases by 1.5%-3%.

The term "prevention" used herein refer to any action that suppresses a disease state of a subject or delays the onset thereof by administration of a pharmaceutical composition according to one aspect.

The term "treatment" used herein refer to any action in which the symptoms of a condition in a subject are improved or beneficially changed due to the administration of a pharmaceutical composition according to one aspect.

The term "muscular aging" used herein refers to the gradual weakening of muscle density and function as mitochondria in muscle fibers lose their activity or the number of mitochondria decreases due to aging. The term "muscular aging" includes sarcopenia.

The term "muscular aging" used in the present disclosure includes the decline of muscles caused by aging, for example, decline in muscle function (grip strength, muscular endurance, muscle power, etc.) or muscle atrophy, and the term "muscular atrophy" refers to the decrease in muscle volume due to the reduction or shrinkage of muscle cells. Due to muscle aging, muscle density and muscle function may gradually deteriorate after the age of 30, and falls and fractures may easily occur. The cause of muscle aging may be a decrease in growth hormone and testosterone, a decrease in the in vitro protein synthesis ability, and a weakened ability to absorb proteins or calories associated with maintaining muscle density.

The term "sarcopenia" used in the present disclosure is a disorder in which the normal amount of muscle, grip strength, and muscle function are decreased due to malnutrition, reduced exercise, and aging. This disorder typically begins to occur in people in their 30s, and in people over the age of 60, muscle mass decreases by around 30%, and by the age of 80, up to half of the muscle mass can be lost.

Sarcopenia causes complications such as diabetes, hyperlipidemia, obesity, etc., and is related to deterioration of overall body function and weakening of bones. In addition, especially in the elderly, as the aging of the spine is closely related to sarcopenia, the probability of developing herniated disks in the lumbar region is very high.

The term "muscle aging-related disorder" used herein refers to a disorder caused by changes in the state of muscles and abnormalities caused by aging. In particular, the muscle loss due to aging is also called age-related sarcopenia.

In an embodiment, the muscle-related disorders may be sarcopenia, geriatric sarcopenia, atony, muscular atrophy, muscular dystrophy, disuse muscle atrophy, motor neuron disease, inflammatory myopathy, neuromuscular junction disease, endocrine myopathy, muscle degeneration, myotonia, muscular atrophy with progressive sclerosis, myasthenia gravis, myositis, muscle calcification, muscle ossification, muscle weakness-related disorders, and cachexia, and are not limited thereto.

The muscle aging-related disorders may be accompanied by muscle inflammation due to trauma, and the composition of the present disclosure has the effect of reducing or alleviating muscle inflammation.

The term "obesity" used herein refers to a condition in which body fat is excessive. The obesity may be clinically a case where the body mass index (BMI) is 25 in Korea, or 30 or more according to the World Health Organization (WHO). In general, obesity refers to a case in which the body weight is higher than a normal value, and even when the body weight is not too much, a case in which the proportion of body fat among the components of the body is high, is referred to as obesity. The obesity may occur in both adults and children. The obesity may cause not only weight gain, but also overeating, excessive drinking and bulimia, hypertension, diabetes, increased plasma insulin concentration, insulin resistance, hyperlipidemia, metabolic syndrome, insulin resistance syndrome, obesity-related gastroesophageal reflux, arteriosclerosis, hypercholesterolemia, hyperuricemia, cardiac hypertrophy and left ventricular hypertrophy, lipodystrophia, non-alcoholic fatty liver disease, cardiovascular disease, or polycystic ovary syndrome. Therefore, the composition may be used for prevention or treatment of not only obesity but also obesity-related disorders. In addition, the composition may be used for subjects who have a desire to lose weight even when they are not obese.

The obesity may be developed due to various causes. For example, the causes may include a high-fat diet, reduced exercise, genetics, psychological factors, endocrine abnormalities, metabolic abnormalities, social and environmental factors. In particular, the obesity may be induced by a high-fat diet.

The composition according to an embodiment may include, based on the total weight of the composition, 0.001 wt % to 80 wt % of *Lactobacillus* sp. mixed strain. In addition, the dosage of *Lactobacillus* sp. mixed strain may be 0.01 mg to 10,000 mg, 0.1 mg to 1000 mg, 1 mg to 100 mg, 0.01 mg to 1000 mg, 0.01 mg to 100 mg, 0.01 mg to 10 mg, or 0.01 mg to 1 mg. The strains may be included in the composition in a therapeutically effective amount or nutritionally effective concentration. For example, one strain, two mixed strains, and three mixed strains may be included in an amount of $10^3$ to $10^{16}$ CFU/g, $10^3$ to $10^{15}$ CFU/g, $10^3$ to $10^{14}$ CFU/g, $10^3$ to $10^{13}$ CFU/g, $10^3$ to $10^{12}$ CFU/g, $10^4$ to $10^{16}$ CFU/g, $10^4$ to $10^{15}$ CFU/g, $10^4$ to $10^{14}$ CFU/g, $10^4$ to $10^{13}$ CFU/g, $10^4$ to $10^{12}$ CFU/g, $10^5$ to $10^{16}$ CFU/g, $10^5$ to $10^{15}$ CFU/g, $10^5$ to $10^{14}$ CFU/g, $10^5$ to $10^{13}$ CFU/g, $10^5$ to $10^{12}$ CFU/g, $10^6$ to $10^{13}$ CFU/g, $10^6$ to $10^{12}$ CFU/g, $10^7$ to $10^{13}$ CFU/g, $10^7$ to $10^{12}$ CFU/g, $10^8$ to $10^{13}$ CFU/g or $10^8$ to $10^{12}$ CFU/g, or cultures of an equivalent number of live bacteria or dead bacteria may be included in the composition. Specifically, in the case of adult patients, $1 \times 10^3$ to $1 \times 10^{16}$ CFU/g of live bacteria or dead bacteria may be administered once or may be divided into several portions which are administered multiple times. However, the dosage may be prescribed in various ways depending on factors such as formulation method, administration method, patient's age, weight and sex, pathological conditions, food, administration time, administration route, excretion rate, and reaction sensitivity, and a person skilled in the art may appropriately adjust the dosage in consideration of these factors. The number of administrations may be once or twice or more within the range of clinically acceptable side effects, and the number of administration sites may be one or two or more. For non-human animals, the same dosage as that for humans per kg of body weight may be administered, or the dosage is calculated based on the volume ratio of organs (such as the heart) between the target animal and humans (for example, the average value) and then administered. Possible routes of administration may include oral, sublingual, parenteral (for example, subcutaneous, intramuscular, intraarterial, intraperitoneal, intrathecal, or intravenous), rectal, topical (including transdermal), inhalation injection, implantable devices, or insertion of substances. Examples of animals to be treated according to an embodiment include humans and other target mammals, and specifically include humans, monkeys, mice, rats, rabbits, sheep, cows, dogs, horses, and pigs. According to one embodiment, the composition includes a killed dry strain, and may be administered in the amount of 1 g to 10 g, 0.5 g to 1.5 g, 2.5 g to 3.5 g, or 4.5 g to 5.5 g once to 3 times a day.

A pharmaceutical composition according to an embodiment may include a pharmaceutically acceptable carrier and/or additives. For example, the pharmaceutical composition may include sterile water, physiological saline, common buffers (phosphoric acid, citric acid, other organic acids, etc.), stabilizers, salts, antioxidants (ascorbic acid, etc.), surfactants, suspending agents, tonicity agents, or preservatives, etc. For topical administration, the pharmaceutical composition may be combined with organic substances such as biopolymers, or inorganic substances such as hydroxyapatite, specifically, collagen matrices, polylactic acid polymers or copolymers, polyethylene glycol polymers or copolymers, and chemical derivatives thereof. When the pharmaceutical composition according to an embodiment is prepared in a formulation suitable for injection, *Lactobacillus* sp. cells may be dissolved or dispersed in a pharmaceutically acceptable carrier, or frozen in such a solution state that they are dissolved or dispersed.

The pharmaceutical composition according to an embodiment, if necessary, depending on the administration method or dosage form, may appropriately include suspending agents, solubilizing agents, stabilizers, isotonic agents, preservatives, anti-adsorption agents, surface-active agents, diluents, disintegrants, pH adjusting agents, analgesics, buffering agents, reducing agents, and antioxidants. Pharmaceutically acceptable carriers and preparations suitable for the present disclosure, including those exemplified above, are described in detail in the document [Remington's Pharmaceutical Sciences, 19th ed., 1995]. The pharmaceutical composition according to an embodiment may be formulated in a unit dosage form or by inserting into a multi-dose container. by using a pharmaceutically acceptable carrier and/or excipient according to a method that can be easily performed by a person skilled in the art to which the present invention pertains. The dosage form may be in the form of a solution, suspension or emulsion in an oil or aqueous medium, or in the form of a powder, granule, tablet or capsule.

The pharmaceutical composition is administered in a pharmaceutically effective amount. The term "pharmaceutically effective amount" used herein refers to an amount sufficient to treat a disease with a reasonable benefit/risk ratio applicable to medical treatment, and the effective dose level may be determined depending on the type, severity, drug activity, sensitivity to the drug, time of administration, route of administration and excretion rate, duration of treatment, drugs used concurrently, and other factors well known in the medical field. The composition of the present disclosure may be administered as an individual therapeutic agent or in combination with other therapeutic agents, may be administered sequentially or simultaneously with conventional therapeutic agents, and may be administered as a single or multiple doses. Considering all of these factors, the minimum effective amount that achieves maximum efficacy without any side effects, which can be easily determined by a person skilled in the art.

Another aspect is to provide a health functional food for preventing or alleviating muscle-related disorders or obesity containing, as an active ingredient, a composition including at least one, two, or three or more selected from the group consisting of: one of a *Lactobacillus fermentum* GB102 strain belonging to *Lactobacillus* sp. deposited with accession number KCTC 14105BP, a lysate thereof, and a culture solution thereof; one of a *Lactobacillus fermentum* GB103 strain belonging to *Lactobacillus* sp. deposited with accession number KCTC 14106BP, a lysate thereof, and a culture solution thereof; and one of a *Lactobacillus plantarum* GB104 strain belonging to *Lactobacillus* sp. deposited with accession number KCTC 14107BP, a lysate thereof, and a culture solution thereof.

In an embodiment, the health functional food may further include a carrier that is acceptable from a food science perspective.

The wording "that is acceptable from a food science perspective" used herein refers to characteristics that are not toxic to cells or humans exposed to the compound.

The term "alleviation" used herein may refer to any action that at least reduces a parameter related to the condition being treated, for example, the severity of a symptom. In this case, the health functional food may be used before or after the onset of the disease, simultaneously with or separately from a drug for treatment, for the prevention or improvement of cancer.

In the health functional food, the active ingredient may be added to food as it is or used together with other food or food ingredients, and may be appropriately used according to conventional methods. The mixing amount of the active ingredient can be suitably determined depending on the purpose of its use (for prevention or alleviation). In general, when preparing food or beverages, the health functional food may be added in an amount of about 15 wt % or less, more specifically about 10 wt % or less, based on the raw material. However, in the case of long-term intake for the purpose of health and hygiene or health control, the amount may be less than these ranges.

The health functional food may be formulated as one selected from the group consisting of tablets, pills, powders, granules, powders, capsules and liquid formulations by further including one or more of carriers, diluents, excipients and additives. Examples of foods to which a compound according to one aspect may be added, include various foods, powders, granules, tablets, capsules, syrups, beverages, gum, tea, vitamin complexes, health functional foods, and the like.

Specific examples of carriers, excipients, diluents, and additives may be at least one selected from the group consisting of lactose, dextrose, sucrose, sorbitol, mannitol, erythritol, starch, acacia gum, calcium phosphate, alginate, gelatin, calcium phosphate, calcium silicate, microcrystalline cellulose, polyvinylpyrrolidone, cellulose, polyvinylpyrrolidone, methylcellulose, water, sugar syrup, methylcellulose, methylhydroxy benzoate, propylhydroxy benzoate, talc, magnesium stearate, and mineral oil.

In addition to containing the active ingredient, the health functional food may contain other ingredients as essential ingredients without particular limitation. For example, like a normal beverage, the health functional food may contain various flavoring agents or natural carbohydrates as additional ingredients. Examples of the natural carbohydrates are: conventional sugars, for example, monosaccharides such as glucose or fructose, disaccharides such as maltose or sucrose, and polysaccharides such as dextrin or cyclodextrin; and sugar alcohols such as xylitol, sorbitol, or erythritol. As flavoring agents other than those described above, natural flavoring agents (thaumatin, *stevia* extract (for example, rebaudioside A, glycyrrhizin, etc.) and synthetic flavoring agents (saccharin, aspartame, etc.) may advantageously be used. The ratio of the natural carbohydrates may be appropriately determined by a person skilled in the art.

In addition to these additives, the health functional food according to one aspect may include various nutrients, vitamins, minerals (electrolytes), flavors such as synthetic flavors and natural flavors, colorants and enhancers (cheese, chocolate, etc.), pectic acid and salts thereof, alginic acid and salts thereof, organic acids, protective colloidal thickeners, pH regulators, stabilizers, preservatives, glycerin, alcohol, and carbonating agents used in carbonated beverages. These components may be used independently or in combination, and the ratio of these additives may also be appropriately selected by a person skilled in the art.

The health functional food may be provided in a mixture with conventionally known health functional food for preventing or alleviating muscle-related disorders or metabolic diseases, or other existing health functional foods. The other health functional food for preventing or alleviating muscle-related disorders or metabolic diseases may be conventionally known health functional food for preventing or alleviating metabolic diseases, existing health functional food, or newly developed health functional food.

When the health functional food includes other health functional food that has an effect of preventing or alleviating muscle-related disorders or metabolic disorders, it is important to mix the amount that can obtain the maximum effect with the minimum amount without side effects, which may be easily determined by a person skilled in the art.

The food composition for preventing or alleviating muscle-related disorders and obesity includes all types of functional foods, nutritional supplements, health foods, and food additives. These types of food composition can be prepared in various forms according to conventional methods known in the art.

The compositions herein may be considered as food supplements. Food supplements, also known as dietary supplements or nutritional supplements, may be considered another particular pharmaceutical product. Food supplements are prepared to supplement the diet and is intended to provide nutrients or beneficial ingredients that may not be consumed or may be consumed in insufficient quantities in a normal diet. Most dietary supplements are considered foods, but sometimes they are considered drugs, natural health products or nutraceutical products. In the sense of the present disclosure, food supplements include health functional foods. Food supplements are usually sold over the counter without a prescription. When food supplements are prepared in the form of pills or capsules, they contain the same excipients used in pharmaceuticals. However, food supplements may also be prepared in the form of foods fortified with some nutrients (for example, infant formula). Thus, in certain embodiments, a composition of the present disclosure is a food supplement.

Compositions according to the present disclosure may be administered as they are or mixed with suitable edible liquids or solids or administered as tablets, pills, capsules, lozenges, granules, powders, suspensions, sachets, syrups, or may be freeze-dried in unit dose form. It may also be in the form of monodoses of the freeze-dried composition to be mixed in a separate liquid container provided together prior to administration.

The composition of the present disclosure may be included in various edible foods and foods, such as milk products in the case of infants. The term "edible product includes, in its broadest sense, any product in any form capable of being consumed by an animal (for example, a product that is able to be accepted by the sense organs). The term "food product" is understood to be an edible product that supplies nutritional support to the body. Foods of particular interest are food supplements and infant formulas. The food preferably includes a carrier material, such as oatmeal gruel, lactic acid fermented foods, resistant starch, dietary fibers, carbohydrates, proteins, and glycated proteins. In some embodiments, the bacterial cells of the present disclosure are homogenized with other ingredients such as cereals or powdered milk to constitute an infant formula.

Another aspect is to provide a feed composition for the preventing or alleviating muscle-related disorders containing, as an active ingredient, a composition including at least one, two, or three or more selected from the group consisting of: one of a *Lactobacillus fermentum* GB102 strain belonging to *Lactobacillus* sp. deposited with accession number KCTC 14105BP, a lysate thereof, a culture solution thereof, and an extract of the culture solution; one of a *Lactobacillus fermentum* GB103 strain belonging to *Lactobacillus* sp. deposited with accession number KCTC 14106BP, a lysate thereof, a culture solution thereof, and an extract of the culture solution; and one of a *Lactobacillus plantarum* GB104 strain belonging to *Lactobacillus* sp. deposited with accession number KCTC 14107BP, a lysate thereof, a culture solution thereof, and an extract of the culture solution.

The feed composition for preventing or alleviating aging-related disorders may be prepared by adding the mixed strain composition in an appropriate effective concentration range according to various feed manufacturing methods known in the art, and may be used as a feed additive for the purpose of preventing or alleviating aging-related disorders.

The "feed" may refer to any natural or artificial formulated feed, one-meal feed, or ingredients of the one-meal feed that an animal eats, ingests, and digests or that is suitable for these. The type of feed is not particularly limited, and feeds commonly used in the art may be used. Non-limiting examples of the feed include: vegetable feeds such as grains, root fruits, food processing by-products, algae, fibers, pharmaceutical by-products, starches, meal or grain by-products; and animal feeds such as proteins, fats, oilseeds, mineral oils, unicellular proteins, zooplankton, or food.

MODE OF DISCLOSURE

Hereinafter, preferred embodiments are presented to help understanding of the present disclosure. However, the following examples are provided to more easily understand the present disclosure, and the content of the present disclosure is not limited by the following examples. Embodiments may be subjected to various modifications, the embodiments are not limited to the embodiments disclosed below and can be implemented in various other forms.

Example 1. Isolation and Identification of *Lactobacillus fermentum* and *Lactobacillus plantarum* Strains 1.1. Isolation of Strains The *Lactobacillus fermentum* strain and the *Lactobacillus plantarum* strain of the present disclosure were isolated from vaginal samples of healthy women who visited a hospital for the purpose of health examination. Specifically, vaginal internal samples were taken with a cotton swab, pre-inoculated on a Rogosa SL (MRS) plate medium, and cultured for 48 hours in an anaerobic chamber at 37° C. When bacterial colonies grew, single colonies were subcultured onto fresh MRS plates for pure isolation. After pure separation, strain culture was performed using MRS medium.

1.2. Selection of Fat Accumulation Inhibitory Active Strains

In order to select strains having fat accumulation inhibitory activity, pancreatic lipase activity and inhibition of differentiation of 3T3-L1 preadipocytes into adipocytes were confirmed.

Specifically, the ability to inhibit the activity of pancreatic lipase was confirmed by diluting the strain of 1-1 to a concentration of 0.1 mg/mL, and adding the same, to a plate, with a solution of 0.167 mM p-nitrophenylpalmitate (PNP; Sigma, USA), 0.061 M Tris-HCl buffer (pH 8.5), and 0.3 mg/mL lipase solution, and causing a reaction at 25° C. for 10 minutes, and then measuring absorbance thereof at 405 nm.

In addition, the ability to inhibit the differentiation of 3T3-L1 preadipocytes into adipocytes was confirmed using Oil Red O (Sigma, USA), which reacts specifically with intracellular fat globules. After adipocyte differentiation was complete, the medium was removed, washed twice with PBS, fixed with 10% formalin at 40° C. for 1 hour, washed twice with 60% isopropanol, and stained with 0.5% Oil Red O solution for 30 minutes at room temperature. After staining, the staining solution was removed and washing was performed twice using distilled water. After the distilled water was completely dried, isopropyl alcohol was added, and the absorbance was measured at 520 nm.

Finally, the 3T3-L1 cell viability of the strain obtained in 1-1 was measured using the 3-(4,5-dimethylthiazol-2-yl)-2, 5-diphenyltetrazolium bromide (MTT) method. 3T3-L1 cells were seeded in a 96-well plate at a concentration of $16 \times 10^4$ cells/well, and the medium was removed after 24 hours of culture. Lactobacillus samples (100, 1,000 μg/mL) diluted at different concentrations were each added to 100 μL of new DMEM medium, followed by 24 hours of culturing. Thereafter, 20 μL of a 5 mg/ml MTT (Sigma, USA) solution was added, and incubated at 37° C. for 4 hours. After culturing, the supernatant was removed, 200 μL of dimethyl sulfoxide (DMSO) was added, and absorbance was measured at 546 nm.

From the results, it was confirmed that each strain had an inhibitory effect on fat accumulation, and from among the prepared strains, *Lactobacillus fermentum* GB102 (hereinafter referred to as 'GB102') and *Lactobacillus fermentum* GB103 (hereinafter referred to as 'GB103') and *Lactobacillus plantarum* GB104 (hereinafter referred to as 'GB104') strains, which showed low cytotoxicity and inhibitory effect on fat cell accumulation, were finally selected. In this regard, the strain name of *Lactobacillus fermentum* was changed to *Limosilactobacillus fermentum*, and the strain name of *Lactobacillus plantarum* was changed to *Lactiplantibacillus plantarum*. In the following examples, the changed strain names of the existing strains were interchangeably described.

1.3. Molecular Biological Identification of Selected Strains

In order to identify the finally selected *Lactobacillus fermentum* strains GB102 and GB103 and *Lactobacillus plantarum* strain GB104, an assay was performed using 16S rRNA gene sequences. The 16S rRNA gene sequences obtained through PCR using 27F and 1492R primers targeting the bacterial 16S rRNA gene were analyzed by the Sanger sequencing method, and the 16s rRNA sequences of *Lactobacillus fermentum* strains GB102 and GB103 and *Lactobacillus plantarum* strain GB104 were represented as sequence listings 1, 2, and 3, respectively.

In addition, homology analysis was performed, and as a result, as shown in Table 1 below, strains GB102 and GB103 had the highest sequence similarity with the standard strain of *Limosilactobacillus fermentum* (type strain), followed by high sequence similarity with *Limosilactobacillus gorilla*. GB104 showed, regarding a 16S rRNA sequence, a sequence similarity of 98% or more to 18 species of the genus *Limosilactobacillus*, including the standard strain of *Lactiplantibacillus plantarum*, and could not be distinguished by 16S rRNA gene sequencing alone. Accordingly, it was confirmed that GB104 is a strain belonging to *Lactiplantibacillus plantarum*, through comparison of genome average nucleotide identity (ANI) values after genome decoding. In conclusion, it was confirmed that the two strains were strains corresponding to *Limosilactobacillus fermentum*, and one strain was a strain corresponding to *Lactiplantibacillus plantarum*.

TABLE 1

| strain | Species | Standard strain name | Sequence similarity (%) |
|---|---|---|---|
| GB102 | Limosilactobacillus fermentum | CECT 562(T) | 99.79 |
|  | Limosilactobacillus gorillae | KZ01(T) | 98.26 |
| GB103 | Limosilactobacillus fermentum | CECT 562(T) | 99.93 |
|  | Limosilactobacillus gorillae | KZ01(T) | 98.13 |
| GB104 | Lactiplantibacillus pentosus | DSM 20314(T) | 99.93 |
|  | Lactiplantibacillus argentoratensis | DSM 16365(T) | 99.87 |
|  | Lactiplantibacillus plantarum | ATCC 14917(T) | 99.87 |
|  | Lactiplantibacillus paraplantarum | DSM 10667(T) | 99.73 |
|  | Lactiplantibacillus paraplantarum | DSM 10667(T) | 99.66 |
|  | Lactiplantibacillus herbarum | TCF032-E4(T) | 98.92 |
|  | Lactiplantibacillus daoliensis | 116-1A(T) | 98.82 |
|  | Lactiplantibacillus pingfangensis | 382-1(T) | 98.81 |
|  | Lactiplantibacillus daowaiensis | 203-3(T) | 98.75 |
|  | Lactiplantibacillus nangangensis | 381-7(T) | 98.74 |
|  | Lactiplantibacillus plajomi | NB53(T) | 98.72 |
|  | Lactiplantibacillus fabifermentans | DSM 21115(T) | 98.72 |
|  | Lactiplantibacillus garii | FI11369(T) | 98.61 |
|  | Lactiplantibacillus xiangfangensis | LMG 26013(T) | 98.59 |
|  | Lactiplantibacillus modestisalitolerans | NB466(T) | 98.52 |
|  | Lactiplantibacillus mudanjiangensis | 11050(T) | 98.2 |
|  | Lactiplantibacillus songbeiensis | 398-2(T) | 98.19 |
|  | Lactiplantibacillus dongliensis | 218-3(T) | 98.12 |

Example 2. Genomic and Comparative Genomic Analysis of *Lactobacillus fermentum* Strains In order to identify the genome-based species of strains GB102 and GB103 and investigate characteristics thereof, next-generation sequencing technology (NGS) and bioinformatics technology were used to completely decipher the genome sequence of a strain and functions of the genes were inferred. In addition, the specificity of the strains was confirmed through comparative analysis with the completely translated genome sequence of the same species. This strain was cultured for 4 hours in anaerobic conditions at 37° C. in MRS liquid medium, and genomic DNA was extracted from the culture using the MG Genomic DNA purification kit (MGMED, Inc., Korea). To obtain long read data with an average length of 10 kb or more, the PacBio RS II instrument was used for sequencing analysis, while the NovaSeq 6000 instrument was used to produce short read data with high accuracy and a sequence length of less than 500 bp to compensate for the low-accuracy long read data. The long lead data was assembled into a highly complete GB102 and GB103 genome drafts using the SMRT Analysis server's HGAP2 pipeline. SNP and InDel errors that may exist in the assembled draft genome sequence were corrected through long read data and short sequence data. Coding sequences (CDS) were predicted from the completed genome sequence using the Prodigal program, and rRNA and tRNA were predicted using the RFAM tool. Regarding predicted CDSs, a homology search (applying the BLAST algorithm) was performed based on the open UniProt database, GenBank nr database, Subsystem database, PFAM database, and COG database, to predict functions thereof. From *Lactobacillus fermentum* species standard strain B1 28$^T$ (=ATCC 14931$^T$), *Lactobacillus gorillae* standard strain KZ01$^T$, and *Lactobacillus gastricus* standard strain DSM 16045T genome sequences, which are published in GenBank, and genome sequences of strains GB102 and GB103, genome average nucleotide identity was calculated using the Jspecies program. The analysis results showed that strains GB102 and GB103 have ANI values of over 95% with the *Lactobacillus fermentum* standard strain, indicating that strains GB102 and GB103 belong to the same species (Table 2). In addition, it can be seen that the strains GB102 and GB103 are new species that have not been previously isolated and reported because strains GB102 and GB103 do not match 100% with the standard strain. In addition, strains GB102 and GB103 were also identified as different strains due to the large genomic distance. The inventors of the present application named the strains GB102 and GB103 as "*Lactobacillus fermentum* GB102" (accession number: KCTC 14105BP) and "*Lactobacillus fermentum* GB103" (Accession Number: KCTC 14106BP) and deposited the same at the Korean Collection for Type Cultures (KCTC) located in the Korea Research Institute of Bioscience and Biotechnology on Jan. 14, 2020.

TABLE 2

| Strain Name | Genome size (bp) | GC ratio | ANI values | | | | |
|---|---|---|---|---|---|---|---|
| | | | GB102 | GB103 | B1 28 | KZ01 | DSM 16045 |
| GB102 | 2,039,432 | 51.88 | — | 98.43 | 99.14 | 79.31 | 68.77 |
| GB103 | 2,260,513 | 51.25 | 98.51 | — | 98.42 | 79.72 | 69.23 |
| B128 | 1,905,587 | 52.30 | 99.09 | 98.51 | — | 79.42 | 68.66 |
| KZ01 | 1,641,621 | 48.11 | 79.05 | 79.37 | 79.11 | — | 68.07 |
| DSM 16045 | 1,848,461 | 41.64 | 68.22 | 68.38 | 68.02 | 68.18 | — |

Example 3. Genomic and Comparative Genomic Analysis of *Lactobacillus plantarum* Strain In order to identify the genome-based species of GB104 strain and investigate characteristics thereof, next-generation sequencing technology (NGS) and bioinformatics technology were used to completely decipher the genome sequence of a strain and functions of the genes were inferred. In addition, the specificity of the strain was confirmed through comparative analysis with the completely translated genome sequence of the same species. This strain was cultured for 4 hours in anaerobic conditions at 37° C. in MRS liquid medium, and genomic DNA was extracted from the culture using the MG Genomic DNA purification kit (MGMED, Inc., Korea). To obtain long read data with an average length of 10 kb or more, the PacBio RS II instrument was used for sequencing analysis, while the NovaSeq 6000 instrument was used to produce short read data with high accuracy and a sequence length of less than 500 bp to compensate for the low-accuracy long read data. The long lead data was assembled into a highly complete GB104 genome draft using the SMRT Analysis server's HGAP2 pipeline. SNP and InDel errors that may exist in the assembled draft genome sequence were corrected through long read data and short sequence data. CDSs were predicted from the completed genome sequence using the Prodigal program, and rRNA and tRNA were predicted using the RFAM tool. Regarding predicted CDSs, a homology search (applying the BLAST algorithm) was performed based on the open UniProt database, GenBank nr database, Subsystem database, PFAM database, and COG database, to predict functions thereof. The genome of GB104 is summarized in Table 3.

TABLE 3

| Features | Values | % |
|---|---|---|
| Genome size (bp) | 3,247,930 | 100.00 |
| DNA coding (bp) | 2,742,575 | 84.44 |
| DNA G + C (bp) | 1,445,117 | 44.49 |
| Total genes | 3,087 | 100.00 |
| Protein coding genes | 2,990 | 96.86 |
| Genes with function prediction | 2,517 | 81.54 |
| RNA genes | 87 | 2.82 |
| rRNA genes | 16 | 0.52 |
| tRNA genes | 68 | 2.20 |
| Pseudo genes | 10 | 0.32 |

As a result of genome analysis, it was found that this strain possessed the Plantaricin gene group, which is a group of bacteriocin biosynthetic genes related to antibacterial activity found in *Lactobacillus plantarum*. However, it can be seen that this strain is a new species that has not been previously isolated and reported because this strain does not match 100% with the standard strain and the reference strain.

The inventors of the present application named GB104 as "*Lactobacillus plantarum* GB10" (accession number: KCTC 14107BP) and deposited the same at the Korean Collection for Type Cultures (KCTC) located in the Korea Research Institute of Bioscience and Biotechnology on Jan. 14, 2020.

Experimental Example 1. Verification of Antioxidant Efficacy of Mixed Strain (GB102+GB103+GB104) Consisting of *Lactobacillus* sp. Strain DPPH free radical scavenging activity was evaluated to confirm the antioxidant ability of substances containing strains GB102, GB103 and GB104 as active ingredients or substances containing strains and auxiliary ingredients (vitamin B2 and red *ginseng*).

Specifically, the DPPH solution was prepared to be a 0.2 mM solution in 100% methanol. In addition, strains GB102, GB103, and GB104 and *Lacticaseibacillus rhamnosus* GG (formerly *Lactobacillus rhamnosus* GG, positive control) strains were inoculated into MRS liquid medium and cultured at 37° C. at 16-hour intervals. Thereafter, the strain culture solution was centrifuged (3600 rpm, 15 minutes) to obtain cultured *Lactobacillus*, washed twice with 1×PBS, and a mixture of three *Lactobacillus* strains GB102, GB103, and GB104 at a concentration of 5×10$^9$ CFU/mL, was prepared. Similarly, a comparative strain of *Lacticaseibacillus rhamnosus* GG was prepared at a concentration of 5×10$^9$ CFU/ml.

As auxiliary ingredients, samples were prepared with vitamin B2 and red *ginseng* capsule contents at a concentration of 625 μg/mL, and L-ascorbic acid (positive control group) was prepared at a concentration of 12.5 ug/mL.

125 ug (200 ul) of auxiliary ingredients; 1×10$^9$ CFU (200 ul) of a mixture of three *Lactobacillus* strains GB102, GB103, and GB104; a combination of 1×10$^9$ CFU (200 ul) of a mixture of three *Lactobacillus* strains GB102, GB103, and GB104 and 125 ug (200 ul) of auxiliary ingredients were each mixed with 200 ul of 0.2 mM DPPH solution and then caused a reaction in a dark room at room temperature for 30 minutes. Thereafter, 200 µl of the supernatant was obtained by centrifugation (12700 rpm, 5 minutes), and then put into a 96 immunoflat plate and the absorbance at 515 nm was measured using Spectramax iD3 (Molecular devices). As a positive control, 2.5 ug (200 ul) of L-ascorbic acid and $1 \times 10^9$ CFU (200 ul) of *Lacticaseibacillus rhamnosus* GG were used, and as a negative control, PBS (200 ul) was used. The results are shown in Table 4.

DPPH radical scavenging activity was calculated by the following method.

DPPH radical scavenging activity (%)=(OD$_{control}$−OD$_{sample}$)/(OD$_{control}$)×100

OD$_{control}$: Absorbance of PBS, OD$_{sample}$: Absorbance of sample

TABLE 4

|  | L-ascorbic acid | LGG | Red Ginseng + Vitamin B2 | 3 types of *Lactobacillus* | 3 types of *Lactobacillus* + red ginseng + vitamin B2 |
|---|---|---|---|---|---|
| DPPH radical scavenging activity (%) | 53.0 ± 0.37 | 26.2 ± 0.0 | 14.0 ± 0.26 | 44.4 ± 0.26 | 56.2 ± 1.53 |

As shown in Table 4, the DPPH radical scavenging activity efficacy of $1 \times 10^9$ CFU of *Lacticaseibacillus rhamnosus* GG was about 26.2%, and the DPPH radical scavenging activity efficacy of 2.5 ug of L-ascorbic acid was about 53%. The DPPH radical scavenging activity efficacy of 125 µg of the auxiliary ingredients was about 14%, the DPPH radical scavenging activity efficacy of $1 \times 10^9$ CFU of the mixture of three *Lactobacillus* strains GB102, GB103, and GB104 was about 44.4%, and the DPPH radical scavenging activity efficacy of the combination of the mixture of three *Lactobacillus* strains GB102, GB103, and GB104 and 125 ug of the auxiliary ingredients was about 56.2%. Through this, it was confirmed that the mixture of three *Lactobacillus* stains GB102, GB103, and GB104, had superior antioxidant efficacy compared to the positive control *Lactobacillus, Lacticaseibacillus rhamnosus* GG.

The natural process of aging makes the body more susceptible to oxidative damage. Anti-aging effects are mostly related to antioxidant properties and free radical scavenging abilities. Further, the oxidative damage has been proposed as one of the major causes of skeletal muscle decline that occurs with aging. The identification of free radicals as accelerators of the aging process refers to that inhibition of the same can limit the harmful modifications they exert on organisms (particularly skeletal muscle). In other words, when molecules with antioxidant capacity are able to counteract oxidative damage, such molecules could play an important role in preventing the development of aging-related conditions, including the neutralization process. Oxidative damage underlies the pathophysiological mechanism that causes sarcopenia (and other senile diseases), and interventions to enhance endogenous antioxidant defenses (for example, administration of antioxidants) result in inhibition of aging. For example, it has been reported that resveratrol, a polyphenolic compound contained in red wine, can slow down the aging of *Caenorhabditis elegans* due to reduced mitochondrial respiration (Wood et al., 2004). In addition, oxidative stress has been shown to increase bone turnover by causing an imbalance between cells responsible for bone formation and cells responsible for bone resorption. Therefore, since antioxidants are known to inhibit and/or improve the effects of oxidative stress, a mixed strain of *Lactobacillus* sp. according to an embodiment exhibiting antioxidant activity is useful for anti-aging or prevention, alleviation, or treatment of age-related diseases.

Experimental Example 2. Verification of Antioxidant Efficacy of *Lactobacillus* sp. Stains GB102, GB103 and GB104

DPPH free radical scavenging activity was evaluated to confirm the antioxidant capacity of each of strains GB102, GB103 and GB104.

Specifically, a DPPH 0.2 mM solution was prepared using DPPH (Alfa Aesar) reagent in 100% methanol. Strains GB102, GB103, and GB104 and *Lacticaseibacillus rhamnosus* GG (positive control) strains were inoculated into MRS liquid medium and incubated at 37° C. for 16 hours. Thereafter, the strain culture solution was centrifuged (3600 rpm, 15 minutes) to obtain cultured *Lactobacillus*, which was then washed twice with 1×PBS, to prepare a mixture of three *Lactobacillus* stains GB102, GB103, and GB104 at a concentration of $5 \times 10^9$ CFU/ml. Similarly, a comparative strain of *Lacticaseibacillus rhamnosus* GG was prepared at a concentration of $5 \times 10^9$ CFU/ml. $1 \times 10^9$ CFU (200 ul) of each of *Lactobacillus* stains GB102, GB103, and GB104, and $1 \times 10^9$ CFU (200 ul) of a mixture of three *Lactobacillus* stains GB102, GB103, and GB104 were each mixed with 200 µl of a 0.2 mM DPPH solution and reacted for 30 minutes in a dark room at room temperature. Thereafter, 200 µl of the supernatant was obtained by centrifugation (12700 rpm, 5 minutes), and then put into a 96 well-immunoflat and the absorbance at 515 nm was measured using Spectramax iD3 (Molecular devices). DPPH radical scavenging activity was calculated by Experimental Example 1.

TABLE 5

|  | GB102 | GB103 | GB104 | LGG | GB102 + GB103 + GB104 |
|---|---|---|---|---|---|
| DPPH radical scavenging activity (%) | 64.1 ± 1.48 | 41.0 ± 0.28 | 34.5 ± 1.79 | 38.1 ± 0.03 | 53.0 ± 0.20 |

As shown in Table 5, DPPH radical scavenging activities were as follows: GB102 64.1%, GB103 41.0%, GB104 34.5%, *Lacticaseibacillus rhamnosus* GG 38.1%, and GB102+103+104 53%. Through this, it was confirmed that strains GB102, GB103, and GB104 each had an antioxidant effect.

Experimental Example 3. Verification of the Effect of Mixed Strain and/or Herbal Medicine Combination Therapy on Grip Strength Improvement In order to identify the effect of improving grip strength, which had been reduced due to aging, when a mixed strain consisting of *Lactobacillus* sp. strains and/or a co-administration of the same with herbal medicines, old mice was administered with: a mixed strain including *Lactobacillus* stains GB102, GB103, and GB104 (hereinafter referred to as '#7 *Lactobacillus*' or 'mixed strain'); auxiliary ingredients including a mixture of 4 herbal medicines supplemented with inulin and vitamin B2; or a combination of the mixed strain and the auxiliary ingredients, to identify the change in grip strength of aging mice.

The auxiliary ingredients which were co-administered with the mixed strain, included herbal medicines, inulin, and vitamin B2; and Andong yam, adlay, red *ginseng* powder, and *Ganoderma lucidum* were used as herbal medicines. The total content of herbal medicines (Andong yam, adlay, red *ginseng* powder, *Ganoderma lucidum*), inulin, and vitamin B2 was 70.20 mg, and supplementary materials were administered at a total dose of 100.5 mg per mouse, including 30.30 mg of cryopreservative.

TABLE 6

| | Andong Yam | adlay | inulin | Vitamin B2 | red ginseng powder | *Ganoderma lucidum* | Sum |
|---|---|---|---|---|---|---|---|
| Volume | 12.51 mg | 10.10 mg | 18.20 mg | 0.60 mg | 16.28 mg | 12.51 mg | 70.20 mg |

Specifically, as the experimental group, 16-month-old C57BL/6 mice were divided into four groups. Experimental group 1 (G2) was orally administered with a mixed strain (#7 *Lactobacillus*) consisting of *Lactobacillus fermentum* stains GB102 and GB103 strain accession number KTCT 14105BP, KCTC 14106BP), *Lactobacillus plantarum* strain GB104 (accession number KCTC 14107BP). The mixed strain (#7 *Lactobacillus*) was administered at a dose of 5×10⁸ CFU per mouse, and to maintain the guaranteed number of bacteria, the mixed strain was administered together with *Bifidobacterium animalis* sub sp. *Lactis* strain and *Lactobacillus acidophilus*) which were obtained from Mediogen Co., Ltd. Experimental group 2 (G3) was orally administered with auxiliary ingredients including: a herbal medicine mixture consisting of Andong yam, Adlay, Red *ginseng* powder, and *Ganoderma lucidum*, and inulin; and vitamin B2. Auxiliary ingredients were administered at a dose of 100.5 mg per mouse as shown in Table 6 above. Experimental group 3 (G4) was orally co-administered with the mixed strain and auxiliary ingredients. Mice fed with a normal chow diet (NCD) were set as a control. Each of the control and experimental groups consists of 15 mice. The experimental conditions of the experimental groups and the control group are summarized in Table 7 below.

TABLE 7

| Group | Experimental group | Administration substance | Dose | Dosage amount (ml/kg) | N |
|---|---|---|---|---|---|
| G1 | Control | PBS | — | 10 ml/kg | 15 |
| G2 | Mixed strain | Mixed strain | 5 × 10⁸ CFU/head | 10 ml/kg | 15 |
| G3 | Auxiliary ingredients | Auxiliary ingredients | 100.5 mg/head | 10 ml/kg | 15 |
| G4 | Mixed strain + auxiliary ingredients | Mixed strain + auxiliary ingredients | 5 × 10⁸ CFU/head + 100.5 mg/head | 10 ml/kg | 15 |

After each experimental group was administered for 13 weeks, grip strength was measured using a Grip Strength meter by having the mice grip the wire part of the grip strength meter with their front legs and pulling the wire, in order to confirm the improvement of muscle strength. The Results are shown in Table 8.

TABLE 8

| Mean grip strength (%) | Week 0 | Week 11 | Week 13 | Week 16 | Week 21 | Week 26 |
|---|---|---|---|---|---|---|
| PBS | 100 | 77.7 | 72.3 | 82.4 | 84.9 | 85.5 |
| Mixed strain | 100 | 82.5 | 82.1 | 91.3 | 94.6 | 95.4 |
| Auxiliary ingredients | 100 | 81 | 75.7 | 86.3 | 85.8 | 88.7 |
| Mixed strain + auxiliary ingredients | 100 | 102.1 | 104.8 | 114.5 | 116.4 | 122.4 |

As shown in Table 8, compared to control (G1), experimental group 1 (G2), and experimental group 2 (G3), it was confirmed that the grip strength was increased significantly in experimental group 3 (G4), which was co-administered with the mixed strain and auxiliary ingredients.

These results shows that when *Lactobacillus* sp. mixed strain (#7 *Lactobacillus*) and the herbal medicine mixture were administered together, the effect of grip strength, which had been reduced due to aging, is improved.

Experimental Example 4. Verification of Myostatin Measurement Effect in Serum

Myostatin ELISA analysis was performed on serum samples obtained after the necropsy of aging mice fed with the control (PBS), the mixed strain, the auxiliary ingredients, and the combination of the mixed strain and the auxiliary ingredients.

For serum analysis, DGF-8/myostatin DuoSet (R&D systems) ELISA was used, and detailed experimental methods were performed based on the protocol provided by the manufacturer. Briefly, the commonly applied analysis method is as follows: the capture antibody of the product was incubated in a 96-well flat immunoplate (SPL) overnight at 4° C. the day, and then in the next day, washed three times using 0.05% Tween 20 in PBS wash buffer. Thereafter, blocking was performed at room temperature for 1 hour using 1% BSA in PBS sample diluent and washing was performed three times using wash buffer. Samples were diluted according to the dilution factor within the myostatin standard range, and loaded at every 100 ul, and then, incubated for 2 hours at room temperature, and washed 3 times using wash buffer. After incubation of the detection antibody at room temperature for 1 hour, washing was performed 3 times using wash buffer, followed by incubation of streptavidin-HRP for 20 minutes at room temperature and washing 3 times using wash buffer. Finally, a TMB-substrate solution was added thereto and then incubation was performed at room temperature for 20 minutes. Then, 2N $H_2SO_4$ solution was added to stop the reaction, and absorbance at 450 nm was measured using SpectraMax iD3 (Molecular devices) equipment.

TABLE 9

| Group | PBS | Mixed strain | Auxiliary ingredients | Mixed strain + Auxiliary ingredients |
|---|---|---|---|---|
| Mean myostatin (ng/mL) | 4689.8 ± 364.7 | 4439.7 ± 251.2 | 4363.2 ± 200.6 | 3721.8 ± 173.2 |

As shown in Table 9, the results of blood myostatin analysis in serum obtained from aging mice showed were 4689.8±364.7 ng/ml in the case of the control (PBS), 4439.7±251.2 ng/mL when the mixed strain was administered alone, and 4363.2±200.6 ng/ml when auxiliary ingredients were administered alone. The group ingesting the mixed strain and auxiliary ingredients in combination was 3721.8±173.2 ng/ml. Accordingly, it was confirmed that the group ingesting the mixed strain together with the auxiliary ingredients shows a statistically significant decrease in myostatin compared to the group ingesting the mixed strain alone and the group ingesting the auxiliary ingredients alone.

Experimental Example 5. Verification of Intestinal Flora Change, Anti-Aging and Antiobesity Activity in Animal Models by Co-Administration of *Lactobacillus* Mixed Strain and/or Herbal Medicines A total of three groups were used to analyze the intestinal flora change, anti-aging and antiobesity activity induced by the co-administration of *Lactobacillus* mixed strain and/or herbal medicines in aging mice. A group (15 mice) orally administered with phosphate-buffered saline (PBS) to 16-month-old C57BL/6 aging mice for 32 weeks and a group of 10-week-old C57BL/6 young mice (10 mice) were set as controls. In addition, a group of mice (15 mice) orally administered with the mixed strain and auxiliary ingredients used in Experimental Example 2 for 32 weeks to 16-month-old C57BL/6 aging mice was set as the experimental group. After the experiment was completed, each mouse was necropsied, and the cecum was excised and stored frozen at −80° C. Genomic DNA was extracted from frozen samples using FastDNA®SPIN Kit for soil (MP Bio). From each extracted DNA sample, the V3/V4 region of the 16S rRNA gene of the microbial flora was amplified by PCR using 341F and 805R primers (Table 10, SEQ ID NOs: 4 and 5) to which barcode sequences were fused.

TABLE 10

| Primer | Nucleotide sequence (5' → 3') | Sequence number |
|---|---|---|
| 341F | CCT ACG GGN GGC WGC AG | 4 |
| 805R | GAC TAC HVG GGT ATC TAA TCC | 5 |

The amplified product was purified using AMPure XP beads (Beckman). Subsequently, large-capacity nucleotide sequence data was produced from the purified products using the MiSeq (Illumina) platform. Denoising and paired sequence assembly of the large-capacity nucleotide sequence produced was performed using the DADA2 program. OTUs clustering and flora diversity analysis of the sequence-assembled sequence were performed using the published Mothur pipeline (Schloss P D et al. 2009. Introducing mothur: Open-source, platform-independent, community-supported software for describing and comparing microbial communities. Applied and Environmental Microbiology 75:7537-7541). The results are shown in FIGS. 1 to 5.

As shown in FIG. 1, as a result of the flora alpha-diversity analysis based on the 16S rRNA gene sequence, it was confirmed that in the case of the aging mice group, the evenness (Shannon evenness index) of the flora was significantly lower than that of the young mouse group. In the case of the aging mice group subjected to the co-administration of *Lactobacillus* mixed strain and herbal medicines according to an embodiment, there was no significant difference with respect to the young mouse group, but rather, the degree of uniformity of flora was significantly higher than that of the aging mice group. This result indicates that the co-administration of *Lactobacillus* mixed strain and herbal medicines according to an embodiment can have a positive effect on intestinal health by restoring the balance of the intestinal flora in aging animals or preventing the decrease in the balance.

Figure 2:
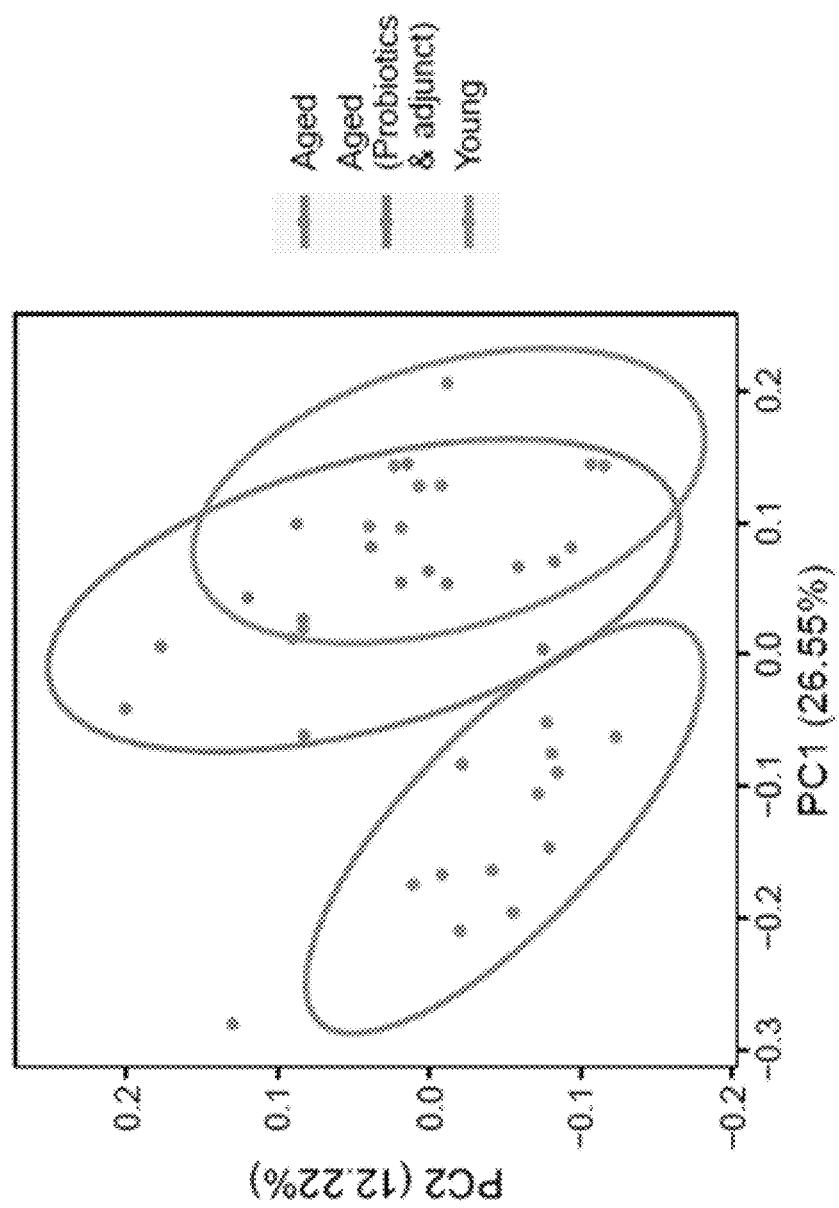
FIG. 2 shows the graph of the principal coordinate analysis (PCoA) results of intestinal flora according to the co-administration of mixed strain and herbal medicines according to an embodiment.

As shown in FIG. 2, a result of principal coordinate analysis (PCoA) of the intestinal flora community structure based on the Weighted-UniFrac distance, it was confirmed that the intestinal flora community of aging mice was different from that of young mice. On the other hand, it was confirmed that the intestinal flora community structure of aging mice co-administered with the mixed strain of *Lactobacillus* and herbal medicine was more similar to that of young mice than that of normal aging mice. This indicates that the co-administration of a *Lactobacillus* mixed strain and herbal medicines according to an embodiment regulates the intestinal flora community structure of aging animals to be similar to that of young animals.

Figure 3:
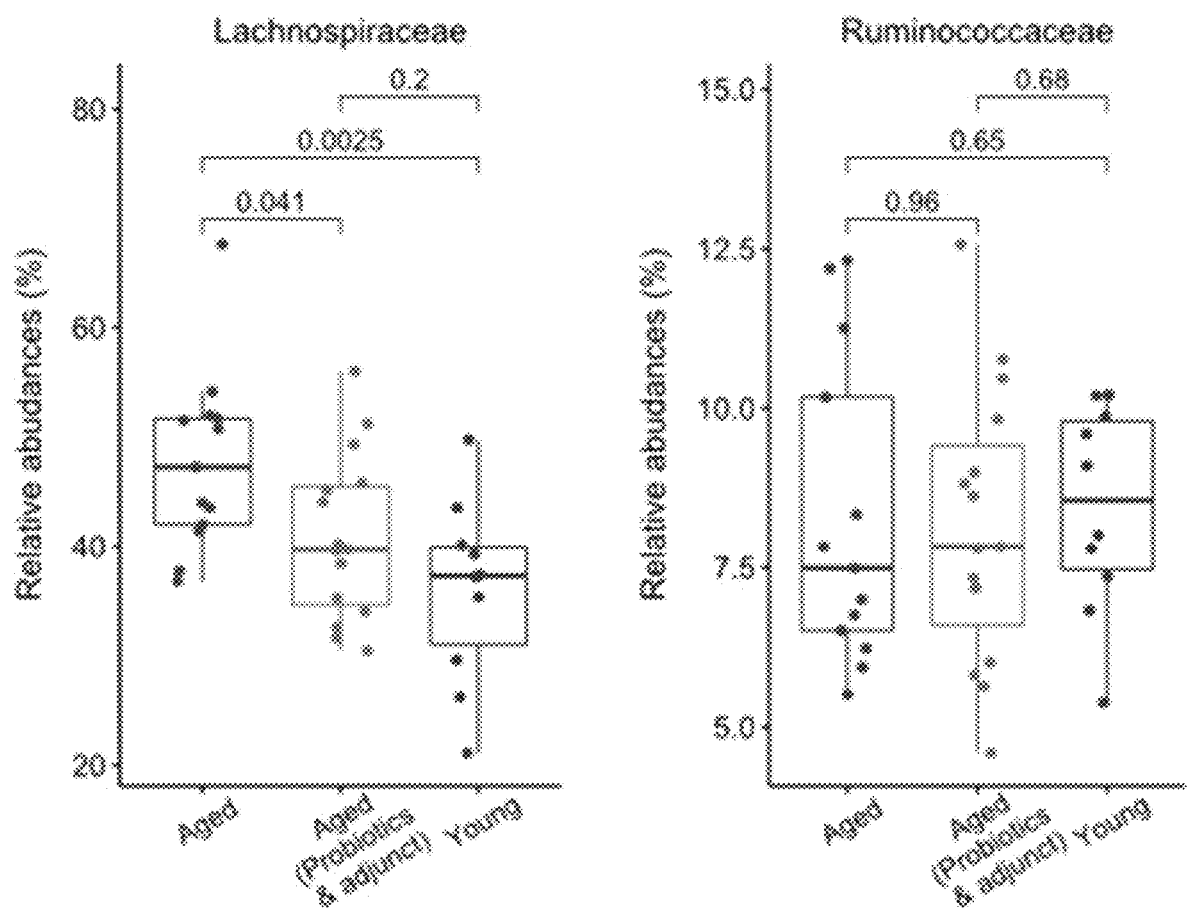
FIG. 3 shows the graph of the frequency difference among major Firmicutes phyla groups according to the co-administration of mixed strain and herbal medicines according to an embodiment.
Figure 4:
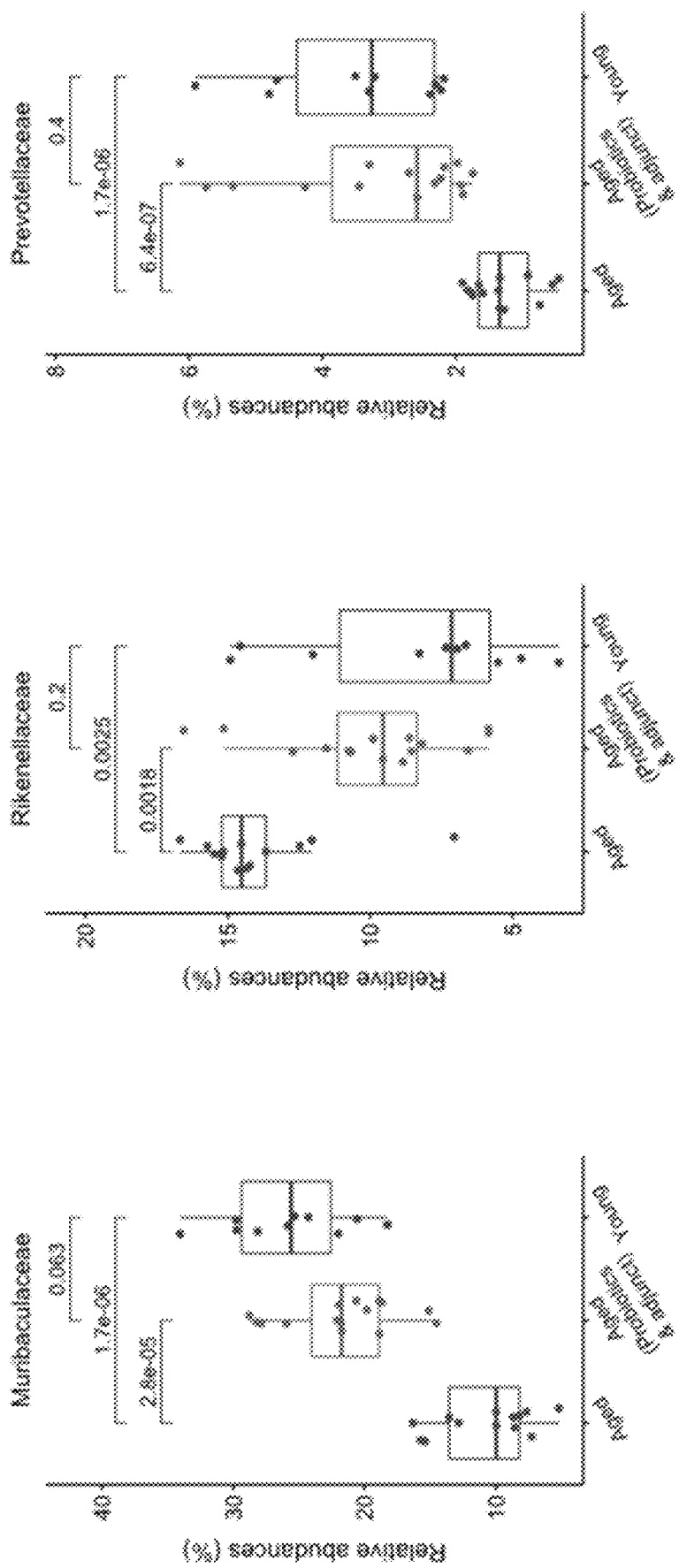
FIG. 4 shows the graph of the frequency difference among major Bacteroidetes phyla groups according to the co-administration of mixed strain and herbal medicines according to an embodiment.

As shown in FIGS. 3 and 4, it was confirmed that the co-administration of a mixed strain and herbal medicines according to an embodiment induces a significant difference in the frequency of major phyla residing in the intestines of aging mice, including Lachnospiraceae, Ruminococcaceae, and Bacteroidetes of the Firmicutes phylum, and Muribaculaceae, Rikenellaceae, and Prevotellaceae of the Bacteroidetes phylum.

Figure 5:
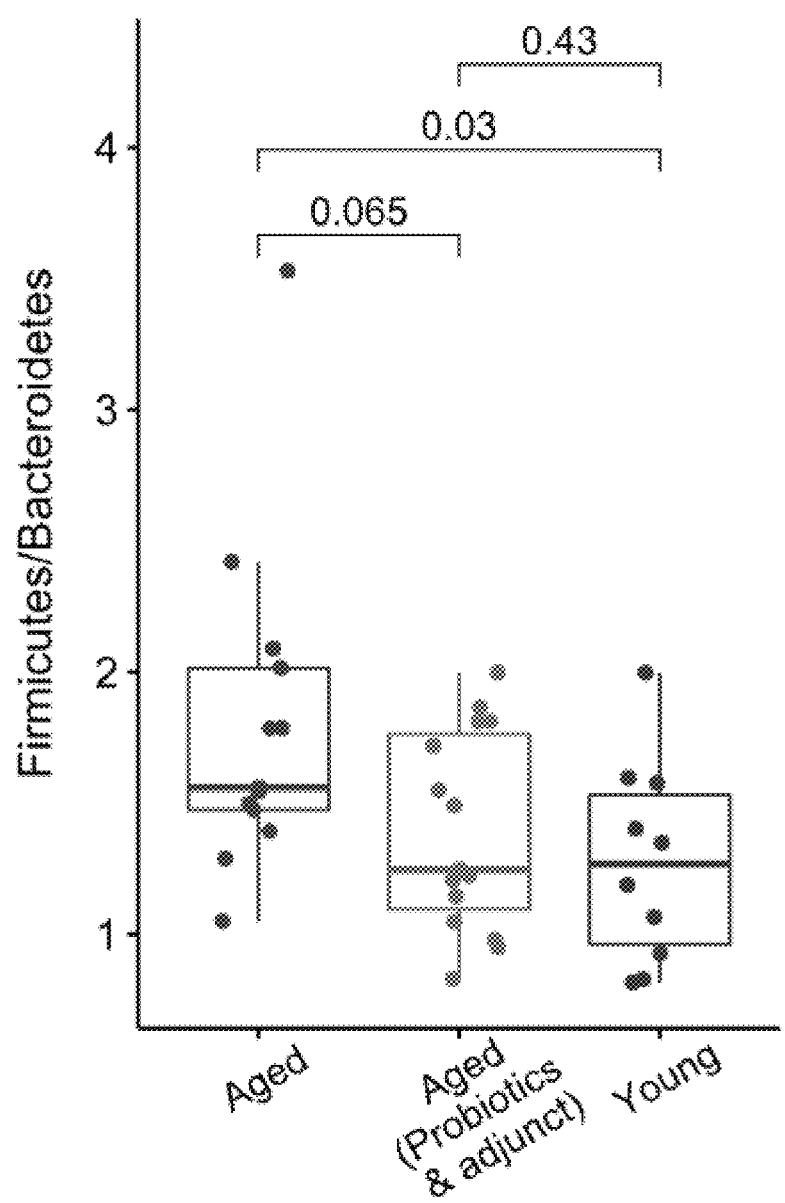
FIG. 5 shows the graph of the ratio changes of Firmicutes/Bacteroidetes according to the administration of mixed strain composition according to an embodiment.

Subsequently, as shown in FIG. 5, the ratio of Firmicutes/Bacteroidetes, which is known as an obesity-related indicator of intestinal flora, showed a significant difference between aging mice and young mice. In an embodiment, it was confirmed that the co-administration of the *Lactobacillus* mixed strain and the herbal medicines changes the intestinal flora of the aging mice to be similar to that of the young mouse, thereby preventing or treating aging-related disorders such as obesity caused by the intestinal flora of the aging mice. In addition, when the *Lactobacillus* mixed strain and herbal medicines were co-administered to aging mice, it was found that the ratio tended to be lower than that of the aging mouse control. In a recent paper, it was reported that the intestinal flora of aging mice can induce obesity, and that the ratio of Firmicutes/Bacteroidetes is increased in aging mice (Binyamin et al., Genome Medicine, 2020). This suggests that the administration of the *Lactobacillus* mixed strain according to an embodiment and herbal medicines may have a positive effect on the prevention and treatment of diseases such as obesity in aging mice.

The above description of the present disclosure is for illustrative purposes, and a person skilled in the art can understand that the embodiments presented herein could be easily modified into other specific forms without changing the technical spirit or essential features of the present disclosure. Therefore, the embodiments described above should be understood as illustrative in all respects and the present disclosure is not limited thereto.

[Accession Numbers]
Name of Depositary Institution: Korea Research Institute of Bioscience and Biotechnology
Accession number: KTCT14105BP
Entrusted date: Jan. 14, 2020
Name of Depositary Institution: Korea Research Institute of Bioscience and Biotechnology
Accession number: KTCT14106BP
Entrusted date: Jan. 14, 2020
Name of Depositary Institution: Korea Research Institute of Bioscience and Biotechnology
Accession number: KTCT14107BP
Entrusted date: Jan. 14, 2020

The invention claimed is:

1. A composition comprising:
a *Lactobacillus fermentum* GB102 strain deposited with Korean Collection for Type Cultures (KCTC) with accession number KCTC 14105BP;
a *Lactobacillus fermentum* GB103 strain deposited with KCTC with accession number KCTC 14106BP;
a *Lactobacillus fermentum* GB104 strain deposited with KCTC with accession number KCTC 14107BP;
a *Bifidobacterium animalis* strain;
a *Lactobacillus acidophilus* strain; and
auxiliary ingredients;
wherein the auxiliary ingredients comprise Andong yam, adlay, *Ganoderma lucidum*, inulin, red *ginseng*, and vitamin B2;
wherein a total amount of the *Lactobacillus fermentum* GB102 strain, the *Lactobacillus fermentum* GB103 strain, the *Lactobacillus fermentum* GB104 strain, the *Bifidobacterium animalis* strain, and the *Lactobacillus acidophilus* strain is $10^8$ CFU/g to $10^{13}$ CFU/g, and
wherein a total amount of the auxiliary ingredients is 70.20 mg.

2. The composition of claim 1, wherein the strains are live bacteria or dead bacteria.

3. The composition of claim 1, wherein the composition is orally administered.

4. The composition of claim 1, wherein the composition is for anti-aging.

5. The composition of claim 4, wherein the anti-aging is one or more selected from the group consisting of anti-aging of muscle cells, anti-aging of nerve cells, anti-aging of skin cells, and anti-aging of an intestinal microbial environment.

6. A health functional food for alleviating muscle disorders, comprising the composition of claim 1 as an active ingredient.

7. The health functional food of claim 6, wherein the composition reduces at least one from the group consisting of joint stiffness, muscle loss, power loss, speed loss, balance loss, endurance loss, and agility loss.

8. The health functional food of claim 6, wherein the composition causes at least one selected from the group consisting of increased exercise performance, restored muscle coordination, restored mobility and gait, and increased muscle mass and grip strength.

9. The health functional food of claim 6, wherein the muscle disorders comprises at least one selected from the group consisting of sarcopenia, geriatric sarcopenia, atony, muscular atrophy, muscular dystrophy, disuse muscle atrophy, motor neuron disease, inflammatory myopathy, neuromuscular junction disease, endocrine myopathy, muscle degeneration, myotonia, muscular atrophy with progressive sclerosis, myasthenia gravis, myositis, muscle calcification, muscle ossification, muscle weakness-related disorders, and cachexia.

10. A pharmaceutical composition for treating muscle disorders comprising the composition of claim 1 as an active ingredient.

11. The pharmaceutical composition of claim 10, wherein the pharmaceutical composition reduces at least one from the group consisting of joint stiffness, muscle loss, power loss, speed loss, balance loss, endurance loss, and agility loss.

12. The pharmaceutical composition of claim 10, wherein the pharmaceutical composition causes at least one selected from the group consisting of increased exercise performance, restored muscle coordination, restored mobility and gait, and increased muscle mass and strength.

13. The pharmaceutical composition of claim 10, wherein the muscle disorders comprise at least one selected from the group consisting of sarcopenia, geriatric sarcopenia, atony, muscular atrophy, muscular dystrophy, disuse muscle atrophy, motor neuron disease, inflammatory myopathy, neuromuscular junction disease, endocrine myopathy, muscle degeneration, myotonia, muscular atrophy with progressive sclerosis, myasthenia gravis, myositis, muscle calcification, muscle ossification, muscle weakness-related disorders, and cachexia.

14. A feed composition comprising the composition of claim 1 as an active ingredient.

* * * * *

SEQUENCE LISTING

<160> NUMBER OF SEQ ID NOS: 5

<210> SEQ ID NO 1
<211> LENGTH: 1441
<212> TYPE: DNA
<213> ORGANISM: Artificial Sequence
<220> FEATURE:
<223> OTHER INFORMATION: GB102 rRNA

<400> SEQUENCE: 1

```
gcaagtcgaa cgcgttggcc caattgattg atggtgcttg cacctgattg attttggtcg      60
ccaacgagtg gcggacgggt gagtaacacg taggtaacct gcccagaagc ggggacaac     120
atttggaaac agatgctaat accgcataac aacgttgttc gcatgaacaa cgcttaaaag    180
atggcttctc gctatcactt ctggatggac ctgcggtgca ttagcttgtt ggtggggtaa    240
tggcctacca aggcgatgat gcatagccga gttgagagac tgatcggcca caatgggact    300
gagacacggc ccatactcct acgggaggca gcagtaggga atcttccaca atgggcgcaa    360
gcctgatgga gcaacaccgc gtgagtgaag aagggtttcg gctcgtaaag ctctgttgtt    420
aaagaagaac acgtatgaga gtaactgttc atacgttgac ggtatttaac cagaaagtca    480
cggctaacta cgtgccagca gccgcggtaa tacgtaggtg gcaagcgtta ccggattta    540
ttgggcgtaa agagagtgca ggcggttttc taagtctgat gtgaaagcct tcggcttaac    600
cggagaagtg catcggaaac tggataactt gagtgcagaa gagggtagtg aactccatg    660
tgtagcggtg gaatgcgtag atatatggaa gaacaccagt ggcgaaggcg ctacctggt    720
ctgcaactga cgctgagact cgaaagcatg ggtagcgaac aggattagat accctggtag    780
tccatgccgt aaacgatgag tgctaggtgt tgagggtttt ccgcccttca gtgccggagc    840
taacgcatta agcactccgc ctggggagta cgaccgcaag gttgaaactc aaaggaattg    900
acggggcccc gcacaagcgg tggagcatgt ggtttaattc gaagctacgc gaagaacctt    960
accaggtctt gacatcttgc gccaacccta gagatagggc gtttccttcg ggaacgcaat   1020
gacaggtggt gcatggtcgt cgtcagctcg tgtcgtgaga tgttgggtta agtcccgcaa   1080
cgagcgcaac ccttgttact agttgccagc attaagttgg gcactctagt gagactgccg   1140
gtgacaaacc ggaggaaggt ggggacgacg tcagatcatc atgccccta tgacctgggc    1200
tacacacgtg ctacaatgga cggtacaacg agtcgcgaac tcgcgagggc aagcaaatct   1260
cttaaaaccg ttctcagttc ggactgcagg ctgcaactcg cctgcacgaa gtcggaatcg   1320
ctagtaatcg cggatcagca tgccgcggtg aatacgttcc cgggccttgt acacaccgcc   1380
cgtcacacca tgagagtttg taacacccaa agtcggtggg gtaaccttt aggagccagc   1440
c                                                                    1441
```

<210> SEQ ID NO 2
<211> LENGTH: 1447
<212> TYPE: DNA
<213> ORGANISM: Artificial Sequence
<220> FEATURE:
<223> OTHER INFORMATION: GB103 rRNA

<400> SEQUENCE: 2

```
atacatgcaa gtcgaacgcg ttggcccaat tgattgatgg tgcttgcacc tgattgattt     60
tggtcgccaa cgagtggcgg acgggtgagt aacacgtagg taacctgccc agaagcgggg    120
gacaacattt ggaaacagat gctaataccg cataacagcg ttgttcgcat gaacaacgct    180
```

```
taaaagatgg cttctcgcta tcacttctgg atggacctgc ggtgcattag cttgttggtg      240
gggtaacggc ctaccaaggc gatgatgcat agccgagttg agagactgat cggccacaat      300
gggactgaga cacggcccat actcctacgg gaggcagcag tagggaatct tccacaatgg      360
gcgcaagcct gatggagcaa caccgcgtga gtgaagaagg gtttcggctc gtaaagctct      420
gttgttaaag aagaacacgt atgagagtaa ctgttcatac gttgacggta tttaaccaga      480
aagtcacggc taactacgtg ccagcagccg cggtaatacg taggtggcaa gcgttatccg      540
gatttattgg gcgtaaagag agtgcaggcg ttttctaag tctgatgtga aagccttcgg      600
cttaaccgga gaagtgcatc ggaaactgga taacttgagt gcagaagagg gtagtggaac      660
tccatgtgta gcggtggaat gcgtagatat atggaagaac accagtggcg aaggcggcta      720
cctggtctgc aactgacgct gagactcgaa agcatgggta gcgaacagga ttagataccc      780
tggtagtcca tgccgtaaac gatgagtgct aggtgttgga gggtttccgc ccttcagtgc      840
cggagctaac gcattaagca ctccgcctgg ggagtacgac cgcaaggttg aaactcaaag      900
gaattgacgg gggcccgcac aagcggtgga gcatgtggtt taattcgaag ctacgcgaag      960
aaccttacca ggtcttgaca tcttgcgcca accctagaga tagggcgttt ccttcgggaa      1020
cgcaatgaca ggtggtgcat ggtcgtcgtc agctcgtgtc gtgagatgtt gggttaagtc      1080
ccgcaacgag cgcaacccct tgttactagtt gccagcatta agttgggcac tctagtgaga      1140
ctgccggtga caaaccggag gaaggtgggg acgacgtcag atcatcatgc cccttatgac      1200
ctgggctaca cacgtgctac aatggacggt acaacgagtc gcgaactcgc gagggcaagc      1260
aaatctctta aaccgttct cagttcggac tgcaggctgc aactcgcctg cacgaagtcg      1320
gaatcgctag taatcgcgga tcagcatgcc gcggtgaata cgttcccggg ccttgtacac      1380
accgcccgtc acaccatgag agtttgtaac acccaaagtc ggtggggtaa cctttagga      1440 gccagcc                                                                1447
```

<210> SEQ ID NO 3
<211> LENGTH: 1552
<212> TYPE: DNA
<213> ORGANISM: Artificial Sequence
<220> FEATURE:
<223> OTHER INFORMATION: GB104 rRNA

<400> SEQUENCE: 3

```
agagtttgat cctggctcag gacgaacgct ggcggcgtgc ctaatacatg caagtcgaac       60
gaactctggt attgattggt gcttgcatca tgatttacat ttgagtgagt ggcgaactgg      120
tgagtaacac gtgggaaacc tgcccagaag cggggggataa cacctggaaa cagatgctaa      180
taccgcataa caacttggac cgcatggtcc gagtttgaaa gatggctttg ctatcacatt      240
ttggatggtc ccgcggcgta ttagctagat ggtggggtaa cggctcacca tggcaatgat      300
acgtagccga cctgagaggg taatcggcca cattgggact gagacacggc ccaaactcct      360
acgggaggca gcagtaggga atcttccaca atggacgaaa gtctgatgga gcaacgccgc      420
gtgagtgaag aagggtttcg gctcgtaaaa ctctgttgtt aaagaagaac atatctgaga      480
gtaactgttc aggtattgac ggtatttaac cagaaagcca ggctaacta cgtgccagca      540 gccgcggtaa tacgtaggtg gcaagcgttg tccggattta ttgggcgtaa agcgagcgca      600
ggcggttttt taagtctgat gtgaaagcct tcggctcaac cgaagaagtg catcggaaac      660
tgggaaactt gagtgcagaa gaggacagtg gaactccatg tgtagcggtg aaatgcgtag      720
```

```
atatatggaa gaacaccagt ggcgaaggcg gctgtctggt ctgtaactga cgctgaggct    780
cgaaagtatg ggtagcaaac aggattagat accctggtag tccataccgt aaacgatgaa    840
tgctaagtgt tggagggttt ccgcccttca gtgctgcagc taacgcatta agcattccgc    900
ctgggagtac ggccgcaagg ctgaaactca aaggaattga cggggggcccg cacaagcggt    960 ggagcatgtg gtttaattcg aagctacgcg aagaaccttta ccaggtcttg acatactatg   1020
caaatctaag agattagacg ttcccttcgg ggacatggat acaggtggtg catggttgtc   1080
gtcagctcgt gtcgtgagat gttgggttaa gtcccgcaac gagcgcaacc cttattatca   1140
gttgccagca ttaagttggg cactctggtg agactgccgg tgacaaaccg gaggaaggtg   1200
ggatgacgtc aaatcatcat gccccttatg acctgggcta cacacgtgct acaatggatg   1260
gtacaacgag ttgcgaactc gcgagagtaa gctaatctct taaagccatt ctcagttcgg   1320
attgtaggct gcaactcgcc tacatgaagt cggaatcgct agtaatcgcg gatcagcatg   1380
ccgcggtgaa tacgttcccg ggccttgtac acaccgcccg tcacaccatg agagtttgta   1440
acacccaaag tcggtgggta accttttagg aaccagccgc ctaaggtggg acagatgatt   1500
agggtgaagt cgtaacaagg tagccgtagg agaacctgcg gctggatcac ct           1552

<210> SEQ ID NO 4
<211> LENGTH: 17
<212> TYPE: DNA
<213> ORGANISM: Artificial Sequence
<220> FEATURE:
<223> OTHER INFORMATION: Primer_341F
<220> FEATURE:
<221> NAME/KEY: misc_feature
<222> LOCATION: (9)..(9)
<223> OTHER INFORMATION: n is a, c, g, or t

<400> SEQUENCE: 4
cctacgggng gcwgcag                                                     17

<210> SEQ ID NO 5
<211> LENGTH: 21
<212> TYPE: DNA
<213> ORGANISM: Artificial Sequence
<220> FEATURE:
<223> OTHER INFORMATION: Primer_805R

<400> SEQUENCE: 5
gactachvgg gtatctaatc c                                                21
```